(12) United States Patent
Li et al.

(10) Patent No.: US 10,098,893 B2
(45) Date of Patent: Oct. 16, 2018

(54) METHODS OF ADMINISTERING A TRACE AMINE-ASSOCIATED RECEPTOR 1 (TAAR1) AGONIST TO PATIENTS HAVING THE MINOR ALLELE OF THE SINGLE NUCLEOTIDE POLYMORPHISM RS2237457

(71) Applicant: Northwestern University, Evanston, IL (US)

(72) Inventors: Jiang Li, Chicago, IL (US); Herbert Y. Meltzer, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/506,253

(22) Filed: Oct. 3, 2014

(65) Prior Publication Data

US 2015/0099741 A1   Apr. 9, 2015

Related U.S. Application Data

(60) Provisional application No. 61/886,288, filed on Oct. 3, 2013.

(51) Int. Cl.

| | |
|---|---|
| *C12Q 1/68* | (2018.01) |
| *C07H 21/04* | (2006.01) |
| *A61K 31/5513* | (2006.01) |
| *A61K 31/137* | (2006.01) |
| *A61K 31/4045* | (2006.01) |
| *C12Q 1/6883* | (2018.01) |

(52) U.S. Cl.
CPC ........ *A61K 31/5513* (2013.01); *A61K 31/137* (2013.01); *A61K 31/4045* (2013.01); *C12Q 1/6883* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 6,316,196 B1 * | 11/2001 | Morten ................ | C12Q 1/6883 435/6.14 |
| 2008/0103179 A1 * | 5/2008 | Tam ...................... | A61K 31/133 514/326 |
| 2014/0155355 A1 * | 6/2014 | McElroy .............. | C07C 217/48 514/114 |

FOREIGN PATENT DOCUMENTS

WO    WO 02/064549    * 8/2002 ............... C12Q 1/68

OTHER PUBLICATIONS

Liou et al. (PLoS ONE, vol. 7, No. 3, pp. e33598, Mar. 2012).*
NCBI dbSNP rs2237457 (2001).*

Zhang et al. (Schizophr Res, vol. 146, No. 0, pp. 285-288, May 2013).*
Rampersaud et al. (Diabetes, vol. 56, pp. 3053-3062, Dec. 2007).*
Arranz B, Rosel P, Ramirez N, Duenas R, Fernandez P, Sanchez JM, et al. Insulin resistance and increased leptin concentrations in noncompliant schizophrenia patients but not in antipsychotic-naive first-episode schizophrenia patients. The Journal of clinical psychiatry 2004; 65(10): 1335-1342.
Bilder RM, Wu H, Bogerts B, Degreef G, Ashtari M, Alvir JM, et al. Absence of regional hemispheric volume asymmetries in first-episode schizophrenia. The American journal of psychiatry 1994; 151(10): 1437-1447.
Conley RR, Kelly DL. Management of treatment resistance in schizophrenia. Biological psychiatry 2001; 50(11): 898-911.
Dao-Castellana MH, Paillere-Martinot ML, Hantraye P, Attar-Levy D, Remy P, Crouzel C, et al. Presynaptic dopaminergic function in the striatum of schizophrenic patients. Schizophrenia research 1997; 23(2): 167-174.
Davis BA, Shrikhande S, Paralikar VP, Hirsch SR, Durden DA, Boulton AA. Phenylacetic acid in CSF and serum in Indian schizophrenic patients. Progress in neuro-psychopharmacology & biological psychiatry 1991; 15(1): 41-47.
Dworkin RH, Lenzenweger MF, Moldin SO, Skillings GF, Levick SE. A multidimensional approach to the genetics of schizophrenia. The American journal of psychiatry 1988; 145(9): 1077-1083.
Elkashef AM, Doudet D, Bryant T, Cohen RM, Li SH, Wyatt RJ. 6-(18)F-DOPA PET study in patients with schizophrenia. Positron emission tomography. Psychiatry research 2000; 100(1): 1-11.
Hietala J, Syvalahti E, Vuorio K, Rakkolainen V, Bergman J, Haaparanta M, et al. Presynaptic dopamine function in striatum of neuroleptic-naive schizophrenic patients. Lancet 1995;346(8983): 1130-1131.
Hietala J, Syvalahti E, Vilkman H, Vuorio K, Rakkolainen V, Bergman J, et al. Depressive symptoms and presynaptic dopamine function in neuroleptic-naive schizophrenia. Schizophrenia research 1999; 35(1): 41-50.
Hitzemann R, Dains K, Bier-Langing CM, Zahniser NR. On the selection of mice for haloperidol response and non-response. Psychopharmacology 1991; 103(2): 244-250.
Ikemoto K, Nishimura A, Oda T, Nagatsu I, Nishi K. Number of striatal D-neurons is reduced in autopsy brains of schizophrenics. Leg Med (Tokyo) 2003; 5 Suppl 1: S221-224.

(Continued)

*Primary Examiner* — Jeanine Anne Goldberg
(74) *Attorney, Agent, or Firm* — Andrus Intellectual Property Law, LLP

(57) ABSTRACT

Disclosed are methods and kits for diagnosing, prognosing, and treating patients having psychiatric disorders. The methods may include assessing whether a patient has a treatment resistant psychiatric disorder or assessing whether the patient is likely to develop a treatment resistant psychiatric disorder. The methods may include detecting genetic markers such as the single nucleotide polymorphism (SNP) in genes present in a genomic nucleic acid sample from the patient, and/or receiving, as a caregiver, the results of tests indicating whether the genetic markers are present in the genomic nucleic acid sample from the patient. The methods may include administering treatment to the patient, for example, based on the detected genetic markers, and administering treatment may include administering new antipsychotic drugs (APDs) that are trace amine-associated receptor 1 (TAAR1) agonists.

11 Claims, 4 Drawing Sheets

(56) References Cited

OTHER PUBLICATIONS

Ji et al., Relationship between three serotonin receptor subtypes (HTR3A, HTR2A and HTR4) and treatment-resistant schizophrenia in the Japanese population, Neuroscience Letters, 2008, 435:95-98.

Jia P, Jayathilake K, Zhao Z, Meltzer HY. Association of FAS, a TNF-alpha receptor gene, with treatment resistant schizophrenia. Schizophrenia research 2011; 129(2-3): 211-212.

Juarez-Reyes MG, Shumway M, Battle C, Bacchetti P, Hansen MS, Hargreaves WA. Effects of stringent criteria on eligibility for clozapine among public mental health clients. Psychiatr Serv 1995; 46(8): 801-806.

Kane J, Honigfeld G, Singer J, Meltzer H. Clozapine for the treatment-resistant schizophrenic. A double-blind comparison with chlorpromazine. Archives of general psychiatry 1988; 45(9): 789-796.

Lindstrom LH, Gefvert O, Hagberg G, Lundberg T, Bergstrom M, Hartvig P, et al. Increased dopamine synthesis rate in medial prefrontal cortex and striatum in schizophrenia indicated by L-(beta-11C) DOPA and PET. Biological psychiatry 1999; 46(5): 681-688.

Maunakea AK, Nagarajan RP, Bilenky M, Ballinger TJ, D'Souza C, Fouse SD, et al. Conserved role of intragenic DNA methylation in regulating alternative promoters. Nature 2010; 466(7303): 253-257.

Meltzer HY, Lee M, Cola P. The evolution of treatment resistance: biologic implications. Journal of clinical psychopharmacology 1998; 18(2 Suppl 1): 5S-11S.

Meltzer HY. Treatment-resistant schizophrenia—the role of clozapine. Current medical research and opinion 1997; 14(1): 1-20.

Meyer-Lindenberg A, Miletich RS, Kohn PD, Esposito G, Carson RE, Quarantelli M, et al. Reduced prefrontal activity predicts exaggerated striatal dopaminergic function in schizophrenia. Nature neuroscience 2002; 5(3): 267-271.

Mouaffak F, Kebir O, Chayet M, Tordjman S, Vacheron MN, Millet B, et al. Association of Disrupted in Schizophrenia 1 (DISC1) missense variants with ultra-resistant schizophrenia. The pharmacogenomics journal 2011; 11(4): 267-273.

Mouaffak F, Kebir O, Bellon A, Gourevitch R, Tordjman S, Viala A, et al. Association of an UCP4 (SLC25A27) haplotype with ultra-resistant schizophrenia. Pharmacogenomics 2011; 12(2): 185-193.

Mukherjee S, Schnur DB, Reddy R. Family history of type 2 diabetes in schizophrenic patients. Lancet 1989; 1(8636): 495.

Mundo E, Altamura AC, Vismara S, Zanardini R, Bignotti S, Randazzo R, et al. MCP-1 gene (SCYA2) and schizophrenia: a case-control association study. American journal of medical genetics Part B, Neuropsychiatric genetics : the official publication of the International Society of Psychiatric Genetics 2005; 132B(1): 1-4.

Neff NH, Wemlinger TA, Duchemin AM, Hadjiconstantinou M. Clozapine modulates aromatic Lamino acid decarboxylase activity in mouse striatum. The Journal of pharmacology and experimental therapeutics 2006; 317(2): 480-487.

Northup A, Nimgaonkar VL. Genetics of schizophrenia: implications for treatment. Expert review of neurotherapeutics 2004; 4(4): 725-731.

O'Reilly R, Davis BA, Durden DA, Thorpe L, Machnee H, Boulton AA. Plasma phenylethylamine in schizophrenic patients. Biological psychiatry 1991; 30(2): 145-150.

Revel FG, Moreau JL, Pouzet B, Mory R, Bradaia A, Buchy D, et al. A new perspective for schizophrenia: TAAR1 agonists reveal antipsychotic- and antidepressant-like activity, improve cognition and control body weight. Molecular psychiatry 2013; 18(5): 543-556.

Ryan MC, Collins P, Thakore JH. Impaired fasting glucose tolerance in first-episode, drug-naïve patients with schizophrenia. The American journal of psychiatry 2003; 160(2): 284-289.

Stern RG, Kahn RS, Davidson M. Predictors of response to neuroleptic treatment in schizophrenia. The Psychiatric clinics of North America 1993; 16(2): 313-338.

Yang W, Tiffany-Castiglioni E, Koh HC, Son IH. Paraquat activates the IRE1/ASK1/JNK cascade associated with apoptosis in human neuroblastoma SH-SY5Y cells. Toxicology letters 2009; 191(2-3): 203-210.

Adkins DE, Aberg K, McClay JL, Bukszar J, Zhao Z, Jia P, et al. Genomewide pharmacogenomic study of metabolic side effects to antipsychotic drugs. Molecular psychiatry 2011; 16(3): 321-332.

Arnaud P, Monk D, Hitchins M, Gordon E, Dean W, Beechey CV, et al. Conserved methylation imprints in the human and mouse GRB10 genes with divergent allelic expression suggests differential reading of the same mark. Human molecular genetics 2003; 12(9): 1005-1019.

Arnold SE, Rioux L. Challenges, status, and opportunities for studying developmental neuropathology in adult schizophrenia. Schizophrenia bulletin 2001; 27(3): 395-416.

Berry MD. The potential of trace animes and their receptors for treating neurological and psychiatric diseases. Reviews on recent clinical trials 2007; 2(1): 3-19.

Borglum AD, Hampson M, Kjeldsen TE, Muir W, Murray V, Ewald H, et al. Dopa decarboxylasegenotypes may influence age at onset of schizophrenia. Molecular psychiatry 2001; 6(6): 712-717.

Bushe C, Holt R. Prevalence of diabetes and impaired glucose tolerance in patients with schizophrenia. The British journal of psychiatry Supplement 2004; 47: S67-71.

Colantuoni C, Lipska BK, Ye T, Hyde TM, Tao R, Leek JT, et al. Temporal dynamics and genetic control of transcription in the human prefrontal cortex. Nature 2011; 478(7370): 519-523.

Dixon LB, et al. Conventional antipsychotic medications for schizophrenia. Schizophrenia bulletin 1995l 21(4): 567-577.

Essock SM, Hargreaves WA, Dohm FA, Goethe J, Carver L, Hipshman L. Clozapine eligibility among state hospital patients. Schizophrenia bulletin 1996; 22(1): 15-25.

Fox CS, Heard-Costa N, Cupples LA, Dupuis J, Vasan RS, Atwood LD. Genome-wide association to body mass index and waist circumference: the Framingham Heart Study 100K project. BMC medical genetics 2007; 8 Suppl 1: S18.

Garfield AS, Cowley M, Smith FM, Moorwood K, Stewart-Cox JE, Gilroy K, et al. Distinct physiological and behavioural functions for parental alleles of imprinted Grb10. Nature 2011; 469(7331): 534-538.

Glessner JT, Reilly MP, Kim CE, Takahashi N, Albano A, Hou C, et al. Strong synaptic transmission impact by copy number variations in schizophrenia. Proceedings of the National Academy of Sciences of the United States of America 2010; 107(23): 10584-10589.

Grunder G, Vernaleken I, Muller MJ, Davids E, Heydari N, Buchholz HG, et al. Subchronic haloperidol downregulates dopamine synthesis capacity in the brain of the schizophrenic patients in vivo. Neuropsychopharmacology: official publication of the American College of Neuropsychopharmacology 2003; 28(4): 787-794.

Guillin O, Abi-Dargham A, Laruelle M. Neurobiology of dopamine in schizophrenia. International review of neurobiology 2007; 78: 1-39.

Hirate Y, Okamoto H. Canopyl, a novel regulator of FGF signaling around the midbrain-hindbrain boundary in zebrafish. Current biology: CB 2006; 16(4): 421-427.

Ji X, Takahashi N, Branko A, Ishihara R, Nagai T, Mouri A, et al. An association between serotonin receptor 3B gene (HTR3B) and treatment-resistant schizophrenia (TRS) in a Japanese population. Nagoya journal of medical science 2008; 70(1-2): 11-17.

Joober R, Benkelfat C, Brisebois K, Toulouse A, Turecki G, Lal S, et al. T102C Polymorphism in the 5HT2A gene and schizophrenia: relation to phenotype and drug response variability. Journal of psychiatry & neuroscience: JPN 1999; 24(2): 141-146.

Kane JM, Honigfeld G, Singer J, Meltzer H. Clozapine in treatment-resistant schizophrenics. Psychopharmacology bulletin 1988; 24(1): 62-67.

Kohlrausch FB, Gama CS, Lobato MI, Belmonte-de-Abreu P, Callegari-Jacques SM, Gesteira A, et al. Naturalistic pharmacogenetic study of treatment resistance to typical neuroleptics in European-Brazilian schizophrenics. Pharmacogentics and genomics 2008; 18(7): 599-609.

(56) References Cited

OTHER PUBLICATIONS

Liou YJ, Wang HH, Lee MT, Wang SC, Chiang HL, Chen CC, et al. Genome-wide association study of treatment refractory schizophrenia in Han Chinese. PloS one 2012; 7(3): e33598.

Liu Y, Li Z, Zhang M, Deng Y, Yi Z, Shi T. Exploring the pathogenetic association between schizophrenia and type 2 diabetes mellitus diseases based on pathway analysis. BMC medical genomics 2013; 6 Suppl 1: S17.

McGowan S, Lawrence AD, Sales T, Quested D, Grasby P. Presynaptic dopaminergic dysfunction in schizophrenia: a positron emission tomographic [18F]fluorodopa study. Archives of general psychiatry 2004; 61(2): 134-142.

Menheniott TR, Woodfine K, Schulz R, Wood AJ, Monk D, Giraud AS, et al. Genomic imprinting of Dopa decarboxylase in heart and reciprocal allelic expression with neighboring Grb10. Molecular and cellular biology 2008; 28(1): 386-396.

Miller GM. The emerging role of trace amine-associated receptor 1 in the functional regulation of monoamine transporters and dopaminergic activity. Journal of neurochemistry 2011; 116(2): 164-176.

Need AC, et al. A Genome-Wide Investigation of SNPs and CNVs in Schizophrenia. PloS Genet. Mar. 2009; 5(3): 10.1371.

Oresic M, Tang J, Seppanen-Laakso T, Mattila I, Saarni SE, Saarni SI, et al. Metabolome in schizophrenia and other psychotic disorders: a general population-based study. Genome medicine 2011; 3(3): 19.

Purcell SM, Wray NR, Stone JL, Visscher PM, O'Donovan MC, Sullivan PF, et al. Common polygenic variation contributes to risk of schizophrenia and bipolar disorder. Nature 20 460(7256): 748-752.

Rampersaud E, Damcott CM, Fu M, Shen H, McArdle P, Shi X, et al. Identification of novel candidate genes for type 2 diabetes from a genome-wide association scan in the Old Order Amish: evidence for replication from diabetes-related quantitative traits and from independent populations. Diabetes 2007; 56(12): 3053-3062.

Reith J, Benkelfat C, Sherwin A, Yasuhara Y, Kuwabara H, Andermann F, et al. Elevated dopa decarboxylase activity in living brain of patients with psychosis. Proceedings of the National Academy of Schiences of the United States of America 1994; 91(24): 11651-11654.

Revel FG, Moreau JL, Gainetdinov RR, Bradaia A, Sotnikova TD, Mory R, et al. TAAR1 activation modulates monoaminergic neurotransmission, preventing hyperdopaminergic and hypoglutamatergic activity. Proceedings of the National Academy of Sciences of the United States of America 2011; 108(20): 8485-8490.

Roussos P, Katsel P, Davis KL, Siever LJ, Haroutunian V. A system-level transcriptomic analysis of schizophrenia using postmortem brain tissue samples. Archives of general psychiatry 2012; 69(12): 1205-1213.

Speight G, Turic D, Austin J, Hoogendoorn B, Cardno AG, Jones L, et al. Comparative sequencing and association studies of aromatic L-amino acid decarboxylase in schizophrenia and bipolar disorder. Molecular psychiatry 2000; 5(3): 327-331.

Terwisscha van Scheltinga AF, Bakker SC, Kahn RS. Fibroblast growth factors in schizophrenia. Schizophrenia bulletin 2010; 36(6): 1157-1166.

Tiihonen J, Wahlbeck K, Lonnqvist J, Klaukka T, Ioannidis JP, Volavka J, et al. Effectiveness of antipsychotic treatments in a nationwide cohort of patients in community care after first hospitalisation due to schizophrenia and schizoaffective disorder: observational follow-up study. BMJ 2006; 333(7561): 224.

van Vlijimen T, Vleugel M, Evers M, Mohammed S, Wulf PS, Heck AJ, et al. A unique residue in rab3c determines the interaction with novel binding protein Zwint-1. FEBS letters 2008; 582(19): 2838-2842.

Wang L, Balas B, Christ-Robers CY, Kim RY, Ramos FJ, Kikani CK, et al. Peripheral disruption of the Grb10 gene enhances insulin signaling and sensitivity in vivo. Molecular and cellular biology 2007; 27(18): 6497-6505.

Zhang JP, Lencz T, Geisler S, Derosse P, Bromet EJ, Malhotra AK. Genetic variation in BDNF is associated with antipsychotic treatment resistance in patients with schizophrenia. Schizophrenia research 2013.

Decision on Appeal dated Aug. 25, 2016 for *Ex Parte Rakesh N. Cheftier, et al.*, for Appeal 2016-003639/ U.S. Appl. No. 13/364,378.

Decision on Appeal dated Jan. 13, 2017 for *Ex Parte Rakesh N. Cheftier, et al.*, for Appeal 2016-003639/ U.S. Appl. No. 13/364,378.

Decision on Appeal dated Jul. 19, 2016 for *Ex Parte Marianne Tuefferd, et al.*, for Appeal 2014-005639/ U.S. Appl. No. 13/131,131.

Federal Register, vol. 79, No. 241, Dec. 16, 2014, Rules and Regulations, pp. 74618-74633.

Final Office Action for U.S. Appl. No. 13/131,131 dated Mar. 7, 2017.

\* cited by examiner

METHODS OF ADMINISTERING A TRACE AMINE-ASSOCIATED RECEPTOR 1 (TAAR1) AGONIST TO PATIENTS HAVING THE MINOR ALLELE OF THE SINGLE NUCLEOTIDE POLYMORPHISM RS2237457

CROSS-REFERENCED TO RELATED PATENT APPLICATIONS

The present application claims the benefit of priority under 35 U.S.C. § 119(e) to U.S. Provisional Patent Application No. 61/886,288, filed on Oct. 3, 2013, the content of which is incorporate herein by reference in its entirety.

BACKGROUND

The invention relates to methods for diagnosing and treating psychiatric disorders in a patient. In particular, the intention relates to methods for identifying genetic markers that are associated with treatment resistant psychiatric disorders and administering a treatment for the treatment resistant psychiatric disorder to the patient based on identifying the genetic markers. The genetic markers may include polymorphisms such as single nucleotide polymorphisms (SNPs) and the alternate treatment may include foregoing administering typical or atypical antipsychotic drugs (APDs), where the patient has been diagnosed with a treatment resistant psychiatric disorder, and instead administering a different treatment regimen or a new APD as disclosed herein.

Psychiatric disorders such as schizophrenia, bipolar disorder, and depression with psychotic features are estimated to affect millions or Americans. Many patients with psychiatric disorders are successfully treated with typical or atypical APDs. For example, following treatment with typical APDs (i.e., first generation APDs) or atypical APDs (i.e., second generation APDs), about 70% of people with schizophrenia have significant remission of positive symptoms.[6,9] However, many patients with psychiatric disorders are resistant to treatment with typical or atypical APDs. For example, about 30% of people with schizophrenia are resistant to treatment with APDs, where treatment resistant schizophrenia (TRS) may be defined as presence of moderate to severe positive symptoms despite treatment with two or more trials of APDs other than clozapine at usually adequate doses for 4-6 weeks.[6] Some population studies have suggested that an even higher proportion of treatment resistant (TR) patients exists.[1-4]

Furthermore, treatment with certain APDs may have undesirable side effects. For example, olanzapine, clozapine, and quetiapine may cause an increased risk of developing metabolic abnormalities such as the impaired glucose metabolism/diabetes and weight gain/obesity.[4,8] As such, if a patient has a treatment resistant psychiatric disorder, administering some APDs is not beneficial and may be detrimental. However, there currently are no available diagnostic tests for predicting whether a patient having a psychiatric disorder will be resistant to treatment with APDs. Here, genetic markers that are associated with treatment resistant psychiatric disorders are identified. By using these genetic markers, clinicians can stratify psychiatric patients based on the markers and provide a more personalized treatment for patients with treatment resistant psychiatric disorders and avoid administering typical or atypical APDs and instead administer a different treatment regimen or a new APD as disclosed herein.

SUMMARY

Disclosed are methods, compositions, and kits for diagnosing, prognosing, and treating psychiatric disorders. The disclosed methods may include identifying genetic markers that may be utilized to diagnose or prognose a patient. Based on identifying the genetic markers, the disclosed methods further may include treating the diagnosed or prognosed patient by not administering a typical or atypical APD and instead administering a different treatment regimen, a APD approved for treating a treatment resistant psychiatric disorder, such as clozapine, or a new APD such as a trace amine-associated receptor 1 (TAAR1) agonist as disclosed herein. The disclosed compositions and kits may include reagents or drugs for diagnosing or prognosing a patient or reagents or drugs for treating a patient.

The disclosed methods and kits may be utilized for diagnosing and treating patients having a treatment resistant psychiatric disorder. The methods may include assessing whether a patient has a treatment resistant psychiatric disorder or assessing the likelihood of the patient developing a treatment resistant psychiatric disorder. The methods may include detecting genetic markers in a genomic nucleic acid sample from the patient and/or receiving (e.g., as a caregiver) results of a test indicating whether a genetic marker has been detected in a genomic nucleic acid sample from the patient. The methods may include detecting, either directly or indirectly, the presence or absence of one or more polymorphisms (e.g., specific single nucleotide polymorphisms (SNPs)) in the genomic nucleic acid sample and/or receiving (e.g., as a caregiver) results of a test indicating whether a polymorphism (e.g., a SNP) is present or absent in the genomic nucleic acid sample. The kits may include reagents for practicing the claimed methods, such as reagents for detecting the specific polymorphisms (e.g., a SNPs), and the reagents of the kits may be configured as an array of reagents.

The polymorphisms detected in the methods or by the kits may include one or more of the following SNPs: rs2237457, rs10825879, rs1421321, rs6763175, rs6500291, rs6924295, rs9675544, rs7085850, rs7933576, rs10047718, rs6043303, rs9313540, rs6432686, rs976760, rs7023648, rs388033, rs4724374, rs12510912, rs6480553, rs12369177, rs7775338, rs6421889, rs3926649, rs12584486, rs17776723, rs1563817, rs9817986, rs9818122, rs13100616, rs7135617, rs11609649, and rs9854706. Specifically, the SNPs detected in the methods or by the kits may include one or more of the following SNPs: rs2237457, rs10825879, rs1421321, rs6763175, rs6500291, rs6924295, and more specifically rs2237457.

In the methods and kits, the minor allele and/or the major allele associated with a SNP may be detected. The methods may include and the kits may be used for determining whether a patient is homozygous or heterozygous for a minor allele and/or major allele associated with a SNP.

In the methods and kits, the SNPs may be detected by any suitable method including biological methods and assays. These may include but are not limited to, nucleotide sequencing, probe hybridization, and primer specific PCR. A reagent for detecting a SNP may include an oligonucleotide that hybridizes specifically to the SNP to form a complex. The oligonucleotide probe further may include a modification or label to detect the hybridization complex. Additionally, a reagent for detecting a SNP may include an oligonucleotide that hybridizes within 100, 50, 20, 10, or 5 nucleotides 5' or 3' of the SNP, for example, where the oligonucleotide is utilized as a primer and detecting comprises sequencing the SNP. The oligonucleotide primer further may include a modification or label to detect the hybridization complex.

In the disclosed methods and kits, the patient may be resistant to treatment with typical APDs (i.e., "first generation" APDs) or atypical APDs (i.e., "second generation" APDs), which may include but are not limited to Benperidol (Anguil®, Benguil®, Frenactil®, Glianimon®), Bromperidol (Bromodol®, Impromen®), Droperidol (Droleptan®, Inapsine®), Haloperidol (Haldol®, Serenace®), Moperone (Luvatren®), Pipamperone (Dipiperon®, Piperonil®), Timiperone (Celmanil®, Tolopelon®), Diphenylbutylpiperidine, Fluspirilene (Imap®), Penfluridol (Semap®), Pimozide (Orap®), Acepromazine (Plegicil®), Chlorpromazine (Largactil®, Thorazine®), Cyamemazine (Tercian®), Dixyrazine (Esucos®), Fluphenazine (Modecate®, Permitil®, Prolixin®), Levomepromazine (Levinan®, Levoprome®, Nozinan®), Mesoridazine (Lidanil®, Serentil®), Perazine (Peragal®, Perazin®, Pernazinum®, Taxilan®), Pericyazine (Neulactil®, Neuleptil®), Perphenazine (Trilafon®), Pipotiazine (Lonseren®, Piportil®), Prochlorperazine (Compazine®), Promazine (Prozine®, Sparine®), Promethazine (Avomine®, Phenergan®), Prothipendyl (Dominal®), Thioproperazine (Majeptil®), Thioridazine (Aldazine®, Mellaril®, Melleril®), Trifluoperazine (Stelazine®), Triflupromazine (Vesprin®), Chlorprothixene (Cloxan®, Taractan®, Truxal®), Clopenthixol (Sordinol®), Flupentixol (Depixol®, Fluanxol®), Tiotixene (Navane®, Thixit®), Zuclopenthixol (Acuphase®, Cisordinol®, Clopixol®), Clotiapine (Entumine®, Etomine®, Etumine®), Loxapine (Adasuve®, Loxitane®), Prothipendyl (Dominal®), Carpipramine (Defekton®, Prazinil®), Clocapramine (Clofekton®, Padrasen®), Molindone (Moban®), Mosapramine (Cremin®), Sulpiride (Meresa®), Sultopride (Barnetil®, Topral®), Veralipride (Agreal®), Amisulpride (Solian®), Amoxapine (Asendin®), Aripiprazole (Abilify®), Asenapine (Saphris®, Sycrest®), Clozapine (Clozaril®), Blonanserin (Lonasen®), Iloperidone (Fanapt®, Fanapta®, Zomaril®), Lurasidone (Latuda®), Melperone (Buronil®, Buronon®, Eunerpan®, Melpax®, Neuril®), Olanzapine (Zyprexa®), Paliperidone (Invega®), Perospirone (Lullan®), Quetiapine (Seroquel®), Remoxipride (Roxiam®), Risperidone (Risperdal®), Sertindole (Serdolect®, Serlect®), Trimipramine (Surmontil®), Ziprasidone (Geodon®, Zeldox®), and Zotepine (Lodopin®, Losizopilon®, Nipolept®, Setous®).

In the disclosed methods, the patient may be administered a treatment for a treatment resistant psychiatric disorder, which may include foregoing administering the typical or atypical ASD based on detecting the SNP and/or receiving results of tests indicating that the SNP is present. Treatments and therapies other than administering typical or atypical ASDs may include but are not limited to administering psychosocial treatment and electroconvulsive therapy, administering a APD approved for treating treatment resistant psychiatric disorders (e.g., clozapine), and/or administering new ASDs as disclosed herein (e.g., trace amine-associated receptor 1 (TAAR1) agonists). Alternatively in the disclosed methods, where the SNP is not detected and/or results are receiving indicating that the SNP is not present, the patient may be administered the typical or atypical ASD.

The results disclosed herein implicate L-Dopa Decarboxylase in psychiatric disorders, in particular, treatment resistant psychiatric disorders such as treatment resistant schizophrenia. As such, the presently disclosed methods also include methods of treating a patient having or at risk for developing a psychiatric disorder (e.g., a treatment resistant psychiatric disorders such as such as treatment resistant schizophrenia) by administering to the patient an agent that modulates L-Dopa Decarboxylase expression or activity (e.g., an agent that increases L-Dopa Decarboxylase expression or activity). Because DCC is an enzyme that is rate-limiting in the synthesis of trace amines and neurotransmitters implicated in psychiatric disorders, the present methods also contemplate treating a patient having or at risk for developing a psychiatric disorder (e.g., a treatment resistant psychiatric disorders such as such as treatment resistant schizophrenia) by administering to the patient an agent that is an agonist of the trace amine-associated receptor 1 (TAAR1) for which trace amines are a ligand.

DETAILED DESCRIPTION

Figure 1:
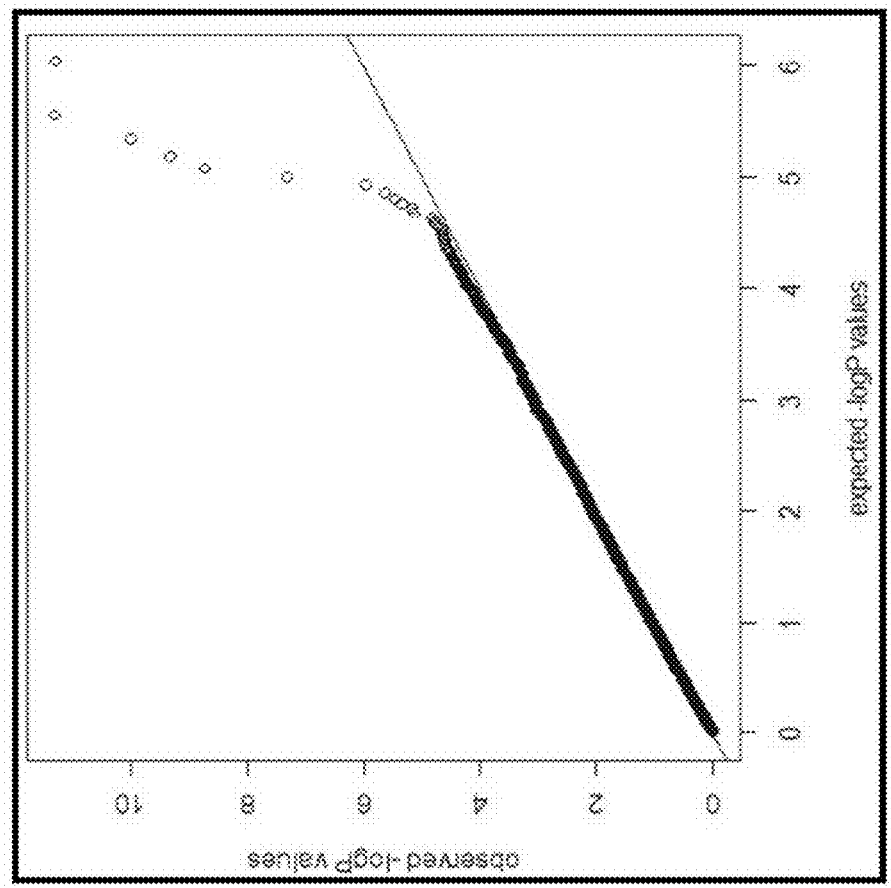
FIG. 1. Quantile-quantile (Q-Q) plot of Genome-wide association with allelic Chi-square test for Caucasian cases with a homozygous genotype for the minor allele of rs2237457.

The present invention is described herein using several definitions, as set forth below and throughout the application.

As used in this specification and the claims, the singular forms "a," "an," and "the" include plural forms unless the content clearly dictates otherwise. For example, "an SNP," should be interpreted to mean "one or more SNPs."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

As used herein, the term "plurality" means "two or more." For example, a "plurality of SNPs" should be interpreted to mean "2, 3, 4, 5 or more SNPs."

As used herein, the term "patient," which may be used interchangeably with the terms "subject" or "individual," refers to one who receives medical care, attention or treatment and may encompass a human patient. As used herein, the term "patient" is meant to encompass a person who has a psychiatric disorder or is at risk for developing a psychiatric disorder, which includes but is not limited to schizophrenia, bipolar disorder, and depression (e.g., depression with psychotic features). For example, the term "patient" is meant to encompass a person at risk for developing schizophrenia or a person diagnosed with schizophrenia (e.g., a person who may be symptomatic for schizophrenia but who has not yet been diagnosed). The term "patient" also is meant to encompass a person at risk for developing bipolar disorder or a person diagnosed with bipolar disorder (e.g., a person who may be symptomatic for bipolar disorder but who has not yet been diagnosed). The term "patient" further is meant to encompass a person at risk for developing depression (e.g., depression with psychotic features). As such, the term "patient" further is meant to encompass a person at risk for developing depression with psychotic features or a person diagnosed with depression with psychotic features (e.g., a person who may be symptomatic for depression with psychotic features but who has not yet been diagnosed).

The term "patient" further is meant to encompass a person at risk for developing a treatment resistant psychiatric disorder, which may include but is not limited to schizophrenia, bipolar disorder, and depression with psychotic features. For example, the term "patient" is meant to encompass a person at risk for developing treatment resistant schizophrenia (TRS) or a person diagnosed with TRS (e.g., a person who may be symptomatic for TRS but who has not yet been diagnosed). The term "patient" also is meant to encompass a person at risk for developing treatment resistant bipolar disorder or a person diagnosed with treatment resistant bipolar disorder (e.g., a person who may be symptomatic for treatment resistant bipolar disorder but who has not yet been diagnosed). The term "patient" further is meant to encompass a person at risk for developing treatment resistant depression (e.g., treatment resistant depression with psychotic features). As such, the term "patient" further is meant to encompass a person at risk for developing treatment resistant depression with psychotic features or a person diagnosed with treatment resistant depression with psychotic features (e.g., a person who may be symptomatic for treatment resistant depression with psychotic features but who has not yet been diagnosed).

As used herein, the term "patient" also is meant to encompass a person who has a psychiatric disorder or is at risk for developing a psychiatric disorder that is associated with increased or decreased biological activity of L-Dopa Decarboxylase (DCC), which is an enzyme that is rate limiting in the synthesis of trace amines and neurotransmitters. For example, a patient having a psychiatric disorder that is associated with decreased biological activity of DCC may be treated by administering an agent that increases biological activity of DCC, and/or an agent that increases expression of DCC. Because DCC is an enzyme that is rate-limiting in the synthesis of trace amines and neurotransmitters implicated in psychiatric disorders, a patient having a psychiatric disorder that is associated with decreased biological activity of DCC may be treated by administering an agent that is an agonist of the trace amine-associated receptor 1 (TAAR1) for which trace amines are a ligand.

A patient may include a patient having or at risk for developing a psychiatric disease or disorder that is resistant to treatment with typical or atypical antipsychotic drugs (APDs). Typical and atypical APDs for treating psychiatric diseases or disorders may include, but are not limited to, drugs such as Benperidol (Anguil®, Benguil®, Frenactil®, Glianimon®), Bromperidol (Bromodol®, Impromen®), Droperidol (Droleptan®, Inapsine®), Haloperidol (Haldol®, Serenace®), Moperone (Luvatren®), Pipamperone (Dipiperon®, Piperonil®), Timiperone (Celmanil®, Tolopelon®), Diphenylbutylpiperidine, Fluspirilene (Imap®), Penfluridol (Semap®), Pimozide (Orap®), Acepromazine (Plegicil®), Chlorpromazine (Largactil®, Thorazine®), Cyamemazine (Tercian®), Dixyrazine (Esucos®), Fluphenazine (Modecate®, Permitil®, Prolixin®), Levomepromazine (Levinan®, Levoprome®, Nozinan®), Mesoridazine (Lidanil®, Serentil®), Perazine (Peragal®, Perazin®, Pernazinum®, Taxilan®), Pericyazine (Neulactil®, Neuleptil®), Perphenazine (Trilafon®), Pipotiazine (Lonseren®, Piportil®), Prochlorperazine (Compazine®), Promazine (Prozine®, Sparine®), Promethazine (Avomine®, Phenergan®), Prothipendyl (Dominal®), Thioproperazine (Majeptil®), Thioridazine (Aldazine®, Mellaril®, Melleril®), Trifluoperazine (Stelazine®), Triflupromazine (Vesprin®), Chlorprothixene (Cloxan®, Taractan®, Truxal®), Clopenthixol (Sordinol®), Flupentixol (Depixol®, Fluanxol®), Tiotixene (Navane®, Thixit®), Zuclopenthixol (Acuphase®, Cisordinol®, Clopixol®), Clotiapine (Entumine®, Etomine®, Etumine®), Loxapine (Adasuve®, Loxitane®), Prothipendyl (Dominal®), Carpiramine (Defekton®, Prazinil®), Clocapramine (Clofekton®, Padrasen®), Molindone (Moban®), Mosapramine (Cremin®), Sulpiride (Meresa®), Sultopride (Barnetil®, Topral®), Veralipride (Agreal®), Amisulpride (Solian®), Amoxapine (Asendin®), Aripiprazole (Abilify®), Asenapine (Saphris®, Sycrest®), Clozapine (Clozaril®), Blonanserin (Lonasen®), Iloperidone (Fanapt®, Fanapta®, Zomaril®), Lurasidone (Latuda®), Melperone (Buronil®, Buronon®, Eunerpan®, Melpax®, Neuril®), Olanzapine (Zyprexa®), Paliperidone (Invega®), Perospirone (Lullan®), Quetiapine (Seroquel®), Remoxipride (Roxiam®), Risperidone (Risperdal®), Sertindole (Serdolect®, Serlect®), Trimipramine (Surmontil®), Ziprasidone (Geodon®, Zeldox®), and Zotepine (Lodopin®, Losizopilon®, Nipolept®, Setous®). A patient having a treatment resistant psychiatric disease or disorder accordingly may include a patient that is resistant to treatment with, for example, any of these foregoing APDs.

In some embodiments of the disclosed methods, the patient may have undergone treatment prior to the disclosed methods being performed and the patient may have been diagnosed with a treatment resistant psychiatric disorder prior to the method being performed. For example, prior to disclosed methods being performed the patient may have been diagnosed and treated for schizophrenia using an antipsychotic drug (APD) selected from the group consisting of Benperidol (Anguil®, Benguil®, Frenactil®, Glianimon®), Bromperidol (Bromodol®, Impromen®), Droperidol (Droleptan®, Inapsine®), Haloperidol (Haldol®, Serenace®), Moperone (Luvatren®), Pipamperone (Dipiperon®, Piperonil®), Timiperone (Celmanil®, Tolopelon®), Diphenylbutylpiperidine, Fluspirilene (Imap®), Penfluridol (Semap®), Pimozide (Orap®), Acepromazine (Plegicil®), Chlorpromazine (Largactil®, Thorazine®), Cyamemazine (Tercian®), Dixyrazine (Esucos®), Fluphenazine (Modecate®, Permitil®, Prolixin®), Levomepromazine (Levinan®, Levoprome®, Nozinan®), Mesoridazine (Lidanil®, Serentil®), Perazine (Peragal®, Perazin®, Pernazinum®, Taxilan®), Pericyazine (Neulactil®, Neuleptil®), Perphenazine (Trilafon®), Pipotiazine (Lonseren®, Piportil®), Prochlorperazine (Compazine®), Promazine (Prozine®, Sparine®), Promethazine (Avomine®, Phenergan®), Prothipendyl (Dominal®), Thioproperazine (Majeptil®), Thioridazine (Aldazine®, Mellaril®, Melleril®), Trifluoperazine (Stelazine®), Triflupromazine (Vesprin®), Chlorprothixene (Cloxan®, Taractan®, Truxal®), Clopenthixol (Sordinol®), Flupentixol (Depixol®, Fluanxol®), Tiotixene (Navane®, Thixit®), Zuclopenthixol (Acuphase®, Cisordinol®, Clopixol®), Clotiapine (Entumine®, Etomine®, Etumine®), Loxapine (Adasuve®, Loxitane®), Prothipendyl (Dominal®), Carpipramine (Defekton®, Prazinil®), Clocapramine (Clofekton®, Padrasen®), Molindone (Moban®), Mosapramine (Cremin®), Sulpiride (Meresa®), Sultopride (Barnetil®, Topral®), Veralipride (Agreal®), Amisulpride (Solian®), Amoxapine (Asendin®), Aripiprazole (Abilify®), Asenapine (Saphris®, Sycrest®), Clozapine (Clozaril®), Blonanserin (Lonasen®), Iloperidone (Fanapt®, Fanapta®, Zomaril®), Lurasidone (Latuda®), Melperone (Buronil®, Buronon®, Eunerpan®, Melpax®, Neuril®), Olanzapine (Zyprexa®), Paliperidone (Invega®), Perospirone (Lullan®), Quetiapine (Seroquel®), Remoxipride (Roxiam®), Risperidone (Risperdal®), Sertindole (Serdolect®, Serlect®), Trimipramine (Surmontil®), Ziprasidone (Geodon®, Zeldox®), and Zotepine (Lodopin®, Losizopilon®, Nipolept®, Setous®). Accordingly, the methods contemplated herein include methods for diagnosing, prognosing, and treating patients with treatment resistant schizophrenia (TRS) where the patient has been observed to be resistant to treatment with any of the aforementioned APDs.

Patients encompassed by the disclosed methods of diagnosis, prognosis, and treatment may include patients having treatment resistant schizophrenia (TRS), where TRS may be defined using generally accepted criteria in the field, for example, as developed by Kane et al. (1988) in the Multicenter Clozapine Trial (MCT).[8] These criteria included: 1) persistent positive psychotic symptoms: item score≥4 (moderate) on at least 2 of 4 positive symptom items on the Brief Psychiatric Rating Scale (BPRS) (rated on a 1-7 scale)— hallucinatory behavior, suspiciousness, unusual thought content, and conceptual disorganization; 2) current presence of at least moderately severe illness as rated by the total BPRS score (score≥45 on the 18-item scale) and a score of ≥4 (moderate) on the Clinical Global Impression (CGI) scale (Guy 1976)[9]; 3) persistence of illness: no stable period of good social and/or occupational functioning within the last 5 years (inability to maintain work and relationships); 4) drug-refractory condition: at least 3 periods of treatment in the preceding 5 years with conventional APDs (from at least 2 chemical classes) at doses≥1000 mg per day of chlorpromazine for 6 weeks, each without significant symptom relief, and failure to improve by at least 20% in total BPRS score or intolerance to a 6-week prospective trial of haloperidol at a dose of 10-60 mg per day. From an operational point of view, only the positive symptom severity, number and duration of clinical trials (two) are utilized for clinical or research purposes. Treatment resistant schizophrenia usually does not respond to increased dosages of APDs or adding adjunctive agents such as benzodiazepines, antidepressants, anticonvulsants or lithium carbonate.

As used herein, a "caregiver" means a person who administers care to a patient. A "caregiver" may include, among others, a physician, physician's assistant, and a nurse. In the disclosed methods, a caregiver may receive the results of a genetic test prior to administering treatment to a patient. For example, a caregiver may receive the results of a test indicating whether the patient possesses a polymorphism, and the caregiver may administer treatment to the patient based on the results of the test. The test indicating whether the patient possesses a polymorphism may be performed by the caregiver and/or the test may be performed another person or testing facility.

As used herein the terms "diagnose" or "diagnosis" or "diagnosing" refer to distinguishing or identifying a disease, syndrome or condition or distinguishing or identifying a person having or at risk for developing a particular disease, syndrome or condition. As used herein the terms "prognose" or "prognosis" or "prognosing" refer to predicting an outcome of a disease, syndrome or condition. The methods contemplated herein include diagnosing a treatment resistant psychiatric disorder in a patient (e.g., diagnosing TRS in a patient). The methods contemplated herein also include determining a prognosis for a patient having a psychiatric disorder (e.g., determining a prognosis for a patient having TRS).

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration. In particular, the methods contemplated herein include treating a patient having or at risk for developing a treatment resistant psychiatric disorder (e.g. treating a patient having TRS).

The present methods may include detecting a SNP in a patient sample. The term "sample" or "patient sample" is meant to include biological samples such as tissues and bodily fluids. "Bodily fluids" may include, but are not limited to, blood, serum, plasma, saliva, cerebral spinal fluid, pleural fluid, tears, lactal duct fluid, lymph, sputum, and semen. A sample may include nucleic acid, protein, or both.

The detected SNP is present in nucleic acid. The term "nucleic acid" or "nucleic acid sequence" refers to an oligonucleotide, nucleotide or polynucleotide, and fragments or portions thereof, which may be single or double stranded, and represents the sense or antisense strand. A nucleic acid may include DNA or RNA, and may be of natural or synthetic origin. For example, a nucleic acid may include mRNA or cDNA. Nucleic acid may include nucleic acid that has been amplified (e.g., using polymerase chain reaction). Nucleic acid may include genomic nucleic acid.

As used herein, the term "assay" or "assaying" means qualitative or quantitative analysis or testing.

As used herein the term "sequencing," as in determining the sequence of a polynucleotide, refers to methods that determine the base identity at multiple base positions or that determine the base identity at a single position.

The term "amplification" or "amplifying" refers to the production of additional copies of a nucleic acid sequence. Amplification is generally carried out using polymerase chain reaction (PCR) technologies known in the art.

The term "oligonucleotide" is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. Oligonucleotides of the method which function as primers or probes are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. Oligonucleotides used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

The present methods and kits may utilize or contain primers, probes, or both. The term "primer" refers to an oligonucleotide that hybridizes to a target nucleic acid and is capable of acting as a point of initiation of synthesis when placed under conditions in which primer extension is initiated (e.g., primer extension associated with an application such as PCR). For example, primers contemplated herein may hybridize to one or more polynucleotide sequences comprising the SNPs disclosed herein. A "probe" refers to an oligonucleotide that interacts with a target nucleic acid via hybridization. A primer or probe may be fully complementary to a target nucleic acid sequence or partially complementary. The level of complementarity will depend on many factors based, in general, on the function of the primer or probe. For example, probes contemplated herein may hybridize to one or more polynucleotide sequences comprising the SNPs disclosed herein. A primer or probe may specifically hybridize to a target nucleic acid (e.g., hybridize under stringent conditions as discussed herein). In particular, primers and probes contemplated herein may hybridize specifically to one or more polynucleotide sequences that comprise the SNPs disclosed herein and may be utilized to distinguish a polynucleotide sequence comprising a minor allele from a polynucleotide sequence comprising the major allele.

An "oligonucleotide array" refers to a substrate comprising a plurality of oligonucleotide primers or probes. The arrays contemplated herein may be used to detect the SNPs disclosed herein.

As used herein, the term "specific hybridization" indicates that two nucleic acid sequences share a high degree of complementarity. Specific hybridization complexes form under stringent annealing conditions and remain hybridized after any subsequent washing steps. Stringent conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

As used herein, a "target nucleic acid" refers to a nucleic acid molecule containing a sequence that has at least partial complementarity with a probe oligonucleotide, a primer oligonucleotide, or both. A primer or probe may specifically hybridize to a target nucleic acid.

The present methods may be performed to detect the presence or absence of the disclosed SNPs. Methods of determining the presence or absence of a SNP may include a variety of steps known in the art, including one or more of the following steps: reverse transcribing mRNA that comprises the SNP to cDNA, amplifying nucleic acid that comprises the SNP (e.g., amplifying genomic DNA that comprises the SNP), hybridizing a probe or a primer to nucleic acid that comprises the SNP (e.g., hybridizing a probe to mRNA, cDNA, or amplified genomic DNA that comprises the SNP), and sequencing nucleic acid that comprises the SNP (e.g., sequencing cDNA, genomic DNA, or amplified DNA that comprises the SNP).

A "polymorphism" refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism (SNP) is the replacement of one nucleotide by another nucleotide at the polymorphic site. Deletion of a single nucleotide or insertion of a single nucleotide also gives rise to single nucleotide polymorphisms. "Single nucleotide polymorphism" preferably refers to a single nucleotide substitution. Typically, between different individuals, the polymorphic site can be occupied by two different nucleotides which results in two different alleles with the most common allele in the population (i.e., the ancestral allele) being referred to as the "major allele" and the less common allele in the population being referred to as the "minor allele." An individual may be homozygous or heterozygous for the major allele or the minor allele of the polymorphism. "Mutation" as utilized herein, is intended to encompass a single nucleotide substitution, which may be recognized as a single nucleotide polymorphism.

The present methods may be performed to determine whether a patient is heterozygous or homozygous for a major or minor allele of a polymorphism (e.g., a SNP). The term "heterozygous" refers to having different alleles at one or more genetic loci in homologous chromosome segments. As used herein "heterozygous" may also refer to a sample, a cell, a cell population or a patient in which different alleles (e.g., major or minor alleles of SNPs) at one or more genetic loci may be detected. Heterozygous samples may also be determined via methods known in the art such as, for example, nucleic acid sequencing. For example, if a sequencing electropherogram shows two peaks at a single locus and both peaks are roughly the same size, the sample may be characterized as heterozygous. Or, if one peak is smaller than another, but is at least about 25% the size of the larger peak, the sample may be characterized as heterozygous. In some embodiments, the smaller peak is at least about 15% of the larger peak. In other embodiments, the smaller peak is at least about 10% of the larger peak. In other embodiments, the smaller peak is at least about 5% of the larger peak. In other embodiments, a minimal amount of the smaller peak is detected.

As used herein, the term "homozygous" refers to having identical alleles (e.g., major or minor alleles of SNPs) at one or more genetic loci in homologous chromosome segments. "Homozygous" may also refer to a sample, a cell, a cell population, or a patient in which the same alleles at one or more genetic loci may be detected. Homozygous samples may be determined via methods known in the art, such as, for example, nucleic acid sequencing. For example, if a sequencing electropherogram shows a single peak at a particular locus, the sample may be termed "homozygous" with respect to that locus.

Suitable SNPs for the presently disclosed methods, kits, and arrays are disclosed, for example in Table 2. The chromosome location and position of the SNP are listed in Table 2. For example, where the SNP referred to by dbSNP reference ID No. rs2237457 is located on chromosome 7, position 50693638, which may be a thymidine (T) in the minor allele, or a cytosine (C) in the major allele.

The present methods contemplate detecting a single nucleotide polymorphism (SNP). For example, the present methods may detect rs2237457 in either one or both alleles of the patient. (See rs2237457 SNP entry at the National Center for Biotechnology Information, which entry is incorporated herein by reference and refers to a C↔T transition at the reference nucleotide position, where the C-allele is the major allele and the T-allele is the minor allele). This SNP previously was assessed in regard to its association with type 2 diabetes.[31] The present methods may detect a T-allele or a C-allele corresponding to the polymorphism (i.e., a T-nucleotide or a C-nucleotide at the position associated with the rs2237457). The present methods may detect whether a patient is homozygous or heterozygous for a T-allele or C-allele (i.e., whether the patient is TT, TC, or CC at the reference nucleotide position for rs2237457).

Specific genetic markers identified in the methods may include the polymorphism rs2237457. Based on the polymorphism being identified in the patient, for example where the patient is homozygous for the T-allele of rs2237457, the patient may be diagnosed as having a treatment resistant psychiatric disorder. As such, the patient may be administered a treatment for a treatment resistant psychiatric disorder, which may include but is not limited to one or more of the following treatments: foregoing administering to the patient a typical or atypical APD, administering to the patient an APD that is approved for treating a treatment resistant psychiatric disorder such as clozapine (e.g., Clozaril® and FazaClo®), and/or administering a new APD having an active ingredient that is a trace amine-associated receptor 1 (TAAR1) agonist.

The present methods may detect the polymorphism directly by analyzing chromosomal nucleic acid having the polymorphic variant sequence. Alternatively, the present method may detect the polymorphism indirectly by analyzing an isoform nucleic acid expressed from the polymorphic variant sequence, an isoform polypeptide expressed from the polymorphic variant sequence, or the expression of another nucleic acid or protein whose expression is regulated by the polymorphic sequence. For example, the present methods contemplate detecting the single nucleotide polymorphism (SNP) rs2237457 (TT, TC, or CC), where the ancestral allele is the C-allele. This reference SNP is located in the gene for growth factor receptor-bound protein 10 (GRB10). As disclosed herein, a 30 kb block flanking rs2237457 in GRB10, which is 70 kb upstream of L-Dopa Decarboxylase (DCC), was identified as an exclusive cis-acting eQTL for DCC in human dorsolateral prefrontal cortex by BrainCloud. Accordingly, the present methods contemplate detecting expression levels of DCC in a patient, and based on detecting reduced expression levels of DCC, administering an agent to the patient that increases expression of DCC. The present methods also contemplate detecting biological activity levels of DCC in a patient, and based on detecting reduced biological activity levels of DCC, administering an agent to the patient that increases biological activity of DCC. Because DCC is an enzyme that is rate-limiting in the synthesis of trace amines and neurotransmitters implicated in psychiatric disorders, the present methods also contemplate detecting biological activity levels of DCC in a patient, and based on detecting reduced biological activity levels of DCC, administering an agent to the patient that is an agonist of the trace amine-associated receptor 1 (TAAR1) for which trace amines are a ligand.

The results disclosed herein implicate L-Dopa Decarboxylase in psychiatric disorders, in particular, treatment resistant psychiatric disorders such as treatment resistant schizophrenia. As such, the presently disclosed methods include methods of treating a patient having or at risk for developing a psychiatric disorder (e.g., treatment resistant psychiatric disorders such as such as treatment resistant schizophrenia) by administering to the patient an agent that modulates L-Dopa Decarboxylase expression or activity (e.g., an agent that increases L-Dopa Decarboxylase expression or activity). Because DCC is an enzyme that is rate-limiting in the synthesis of trace amines and neurotransmitters implicated in psychiatric disorders, the present methods also contemplate treating a patient having or at risk for developing a psychiatric disorder (e.g., a treatment resistant psychiatric disorders such as such as treatment resistant schizophrenia) by administering to the patient an agent that is an agonist of the trace amine-associated receptor 1 (TAAR1) for which trace amines are a ligand.

Regarding TAAR1 agonists, the TAAR1 is a G protein-coupled receptor that in humans is encoded by the TAAR1 gene and is characterized by its ability to bind low-concentration, endogenous monoamines called trace amines and effect increases in cyclic AMP concentrations in the cell. (See Miller, J. Neurochem. 116(2):164-176 (2010); and Lindemann et al. Genomics 85(3):372-85 (2004)) Trace amines typically are found at low concentrations (e.g., 0.1-10 nM concentrations) and constitute less than 1% of total biogenic amines in the mammalian nervous system. (See Zucchi et al., Br. J. Pharmacol. 149(8):967-78 (2006)). These endogenous trace amines include para/meta-tyramine, tryptamine, phenylethylamine, and para/meta-octopamine, which share structural similarities with the three common monoamines: serotonin, dopamine, and norepinephrine. Each ligand has a different potency for TAAR1 (i.e. $EC_{50}$), which may be measured by the trace amine's ability to effect increases in cyclic AMP (cAMP) concentration after the trace amine binds the receptor. In the presently disclosed methods, the agonists for TAAR1 preferably have an $EC_{50}$ for the TAAR1 of less than about 1000 nM, 500 nM, 400 nM, 300 nM, 200 nM, or 100 nM. Suitable TAAR1 agonists for use in the disclosed methods may include, but are not limited to, m-tyramine, p-tyramine, phenethylamine, m-octopamine, p-octopamine, N-methylphenethylamine, N-methyltyramine, phenylethanolamine, synephrine, 3-methoxytyramine, 3-iodothyronamine, tryptamine, N-methyltryptamine, dopamine, norepinephrine, serotonin, histamine, amphetamine, methamphetamine, 3,4-methylenedioxymethamphetamine, 2,5-dimethoxy-4-iodoamphetamine, phenylpropanolamine, alpha-methylphenethylamine, beta-methylphenethylamine, N-methylphenethylamine, 2-methylphenethylamine, 3-methylphenethylamine, 4-methylphenethylamine, (S)-4-[(ethylphenylamino)methyl]-4,5-dihydrooxazol-2-ylamine (RO5166017), (4S)-4-[(2S)-2-phenylbutyl]-4,5-dihydro-1,3-oxazol-2-amine (RO5256390), (4S)-4-[3-fluoro-2methylphenyl]-4,5-dihydro-1,3-oxazol-2-amine (RO5263397), and (4S)-4-[3,4-dichlorophenyl]-4,5-dihydro-1,3-oxazol-2-amine (RO5203648).

Also disclosed herein are kits for performing the disclosed methods. For example, the disclosed kits may include reagents for diagnosing, prognosing, and/or treating a psychiatric disease or disorder in a patient. The presently disclosed kits may include specific reagents such as one or more of: (a) reagents for detecting the genotype of a patient at the polymorphism rs2237457 (e.g., reagents for sequencing nucleic acid comprising rs2237457 and/or reagents for probing nucleic acid comprising rs2237457); and (b) a pharmaceutical agent for treating a psychiatric disease or disorder. The reagents in the kit may include nucleic acid reagents (e.g., primers and/or probes) and non-nucleic acid reagents (e.g., polymerases and buffers). The pharmaceutical agent of the kits may include an atypical drug for treating the psychiatric disease or disorder such as a TAAR1 agonist formulated for administration to the patient or clozapine formulated for administration to the patient.

EXAMPLES

The following examples are illustrative and are not intended to limit the claimed subject matter.

A Genetic Locus in 7p12.2 Associated with Treatment Resistant Schizophrenia

Abstract

Identifying biomarkers for treatment resistant schizophrenia (TRS) could assist decision making regarding antipsychotic drug (APD) treatment and clarification of the homogeneity of TRS. We conducted a genome-wide association study (GWAS) of Caucasian patients with schizophrenia (79 TR and 95 non-TR). Rs2237457 had the lowest p value in an allelic association test (p=5.53×10-6); it is located in 7p12.2 with reported imprinted inheritance. Haploview disclosed a 30 kb block flanking this SNP in GRB100, 70 kb upstream of L-Dopa Decarboxylase (DDC), an enzyme which is rate limiting in the synthesis of trace amines and neurotransmitters implicated in schizophrenia. The association with TRS improved to $p<10^{-11}$ after excluding heterozygotes, justified by unclear inheritance of the risk allele. This SNP or haplotype was identified as an exclusive cis-acting eQTL for DDC in human dorsolateral prefrontal cortex by BrainCloud. A replication sample produced a weaker result, but in the same direction. Rs2237457 may provide an initial screening test to identify Caucasian TRS and implicates trace amines in the pathophysiology of TRS.

1. Introduction

It is estimated that 1% of the adult population meets current criteria for schizophrenia. Following treatment with typical or atypical antipsychotic drugs (APDs), about 70% of people with schizophrenia have significant reductions in delusions and hallucinations, core psychotic symptoms. The other 30% of schizophrenia patients are referred to as treatment resistant (TRS) or refractory schizophrenia.[1-4] TRS is operationally defined as persistence of moderate to severe positive symptoms despite two or more trials of 4-6 weeks duration with typical or atypical APDs other than clozapine, the only drug approved for TRS.[5,6] Although most TRS patients are cognitively impaired, and have mild to severe negative symptoms, poor outcome, or unresponsive negative symptoms and cognitive impairment, these features are not the basis for TRS as defined here. The frequency and severity of these dimensions of schizophrenia are similar in TRS and non-TRS schizophrenia.[7]

Excluding inadequate APD trials, TRS may result from pharmacodynamic or pharmacokinetic reasons. The latter are rare and will not be considered here. Since schizophrenia is a heterogeneous, complex disease, differences in the cause of psychosis could be the basis for difference in drug response, suggesting TRS is also heterogeneous, specifically due to various genetic or epigenetic factors. During the past decade, there has been a dramatic increase in GWAS studies in schizophrenia to identify risk genes, including genes associated with specific phenotypes and endophenotypes. This approach permits interrogation of the entire human genome at high resolution and high throughput in small to large number of unrelated individuals, unconstrained by prior hypotheses, as is the case with a candidate gene approach. The latter may lead to an incomplete (biased) identification of the biologic pathways relating genes to the trait.

Previous GWAS or candidate gene studies have sought to identify genetic marker(s) of treatment resistance. SNPs, structural variants, or haplotypes in DISC1,[8] UCP4 (SLC25A27),[9] MCP-1(SCYA2),[10] CYP3A5,[11] DRD3,[11] HTR2A,[12] HTR3A,[13] HTR3B,[14] SLAMF1,[15] NFKB1,[15] FAS,[16] BDNF,[17] and others have been reported to be associated with TRS. The reported effect sizes are generally small and have yet to be replicated. Patients with TRS have been reported to have increased cortical atrophy on magnetic resonance imaging (MRI) compared with patients who respond to treatment.[18,19] Cortical atrophy may be due to deficits in neurogenesis, synaptic plasticity, and neurodegeneration. Genes which encode proteins that affect neurogenesis, synaptogenesis, axonal guidance, dendritic spine formation, and synaptic plasticity have been shown to be risk genes for schizophrenia[20,21] and could also be candidate genes for TRS.

In this study, GWAS was initially used to identify genetic markers for TRS in Caucasians, based upon persistence of positive symptoms despite two or more adequate trials. A specific genomic locus or haplotype in intron 4 of growth factor receptor-bound protein 10 (GRB10) was found to be associated with TRS, stimulating an expanded follow-up analysis. BrainCloud, a well-established gene expression database based upon dorsal lateral prefrontal cortex (DLPFC) from the general population, was used to test whether identified genetic markers were related to gene expression changes.[22] More information is available at the Lieber Institute for Brain Development's website.

2. Methods and Materials 2.1 Subjects and Phenotypes

Written informed consent was obtained from all patients after a full description of the risks and benefits of participation. The GWAS included 174 self-described Caucasian patients diagnosed with schizophrenia or schizoaffective disorder by DSM-IV criteria. They were recruited between 1999 and 2010 at clinical facilities associated with Departments of Psychiatry at Case Western Reserve University and Vanderbilt University. The subjects selected for GWAS had participated in prospective clinical trial or longitudinal study of the effect of clozapine. An additional 195 subjects with these diagnoses who had been prospectively classified as TR or NTR were identified from our sample bank for genotyping to obtain additional data. Nearly all of these patients had participated in prospective clinical trials. All study procedures were approved by the Institute Review Boards of the two universities. The data used for classification as TR or NTR, as well as diagnosis, were based upon research interviews supervised and reviewed by one of us (HYM), as well as all available medical records and interviews with significant others when possible.[5,6]

2.2 Genotyping

Genome-wide SNP genotyping was performed using Illumina 610K quad BeadChip® (Illumina, San Diego, Calif., USA) by the Center for Human Genome Variation at Duke University (Durham, N.C., USA). Genotype calling was determined by Illumina GenomeStudio® software (Illumina) using default parameters. Taqman® assay for the top 5 hits was performed on an ABI 7900HT Sequence Detection System (Applied Biosystems, Foster City, Calif., USA) at Northwestern University Genomic Core Facility (Chicago, Ill., USA). Taqman Genotyper Software (Applied Biosystems) was used to do allelic discrimination end-point analysis. Concordance rates between Taqman assay and Illumina GWAS data for the selected top five SNPs was 100%.

2.3 GWAS Data Analysis

All GWAS quality control and association testing was conducted with PLINK 1.0.7 software[23] (more information available at the PLINK website). In addition to the individual SNP, haplotype-based association testing was also conducted. Other statistical analysis was performed by SPSS. Genotype-phenotype association study was carried out by comparing the frequencies of alleles or genotypes between the TR and NTR groups using the following methods: allelic and genotypic association by Pearson's Chi-square, Cochran-Armitage Trend test, or Logistic regression with multiple covariates. Computer corrected significance values (FDR-BH) were calculated. Linkage disequilibrium (LD) was determined with Haploview (more information available at the Broad Institute's website. SNP imputation was achieved with default settings using PUNK binary file sets of the Hapmap genotype data (release 22) available for download at the PLINK website. The same HapMap CEU reference data (2,543,887 SNPs) were used for all imputations. SNPs with A/T or C/G transitions which have a potential to go unflagged by flip command are eliminated. A combined imputation and association analysis of case/control study was performed. SNP Annotation and Proxy Search (SNAP) (more information available at the Broad Institute's website) was also used to search SNPs in LD from 1000 Genome Database or Hapmap database.

QUANTO 1.2 was used to calculate the power of the test more information available from the University of Southern California's website).

2.4 Mapping Cis eQTL and Cis Regulatory Elements

BrainCloud provides genome-wide gene expression data and genetic control based upon a study of human postmortem DLPFC from 109 postnatal Caucasian subjects from prenatal period and throughout the life span.[22] We included all SNP loci within 200 kb interval (100 kb up- and downstream) of transcripts/genes which were found to be associated with TR. ENCODE (more information available at the University of California-Santa Cruz's website and UCSF Brain Methylation Database[24] were applied for prediction of identified genetic variants function as cis regulatory elements.

3. Results 3.1 Clinical Characteristics and Demographic Feature of TR Vs NTR.

Clinical characteristics and demographic feature for the GWAS sample: TR (n=79) and NTR (n=95) patients, and for the additional subjects who were genotyped (TR: n=70 and NTR: n=125) are reported in Table 1.

TABLE 1

Demographic and clinical features for patients who are self-described Caucasians.

| Characteristics | GWAS sample | | Additional sample | | P value |
|---|---|---|---|---|---|
| TR status | TR (N = 79) | NTR (N = 95) | TR (N = 70) | NTR (N = 125) | (GWAS/Additional) |
| Male (%) | 53(67.09%) | 63(66.32%) | 45(64.29%) | 79(63.20%) | 0.914/0.680* |
| Age of first onset (years) | 20.37 ± 0.75 | 22.55 ± 0 83 | 19.71 ± 1.29 | 20.94 ± 0.76 | 0.056/0.380# |
| SubDiagnosis | 69(67.34%) - Schizophrenia 10(12.66%) - Schizoaffective | 64(67.37%) - Schizophrenia 31(32.63%) - Schizoaffective | 38(54.29%) - Schizophrenia 32(45.71%) - Schizoaffective | 48(36.80%) - Schizophrenia 79(63.20%) - Schizoaffective | 0.002/0.018* |
| BPRS | 32.96 ± 1.41 | 26.12 ± 1.11 | 31.37 ± 1.02 | 22.42 ± 1.17 | <0.001/<0.001# |
| BPOS | 11.75 ± 0.61 | 8.42 ± 0.46 | 11.04 ± 0.42 | 6.62 ± 0.48 | <0.0001/<0.0001# |
| BMI | 26.68 ± 0.68 | 28.77 ± 0.79 | 29.11 ± 0.90 | 30.68 ± 1.00 | 0.002/0.219$ |

Data was presented as Mean ± SE.
*Chi-square test;
t-test;
$ANCOVA test adjusted by Gender.
BPRS represents Brief Psychiatric Rating Scale.
BPOS is the sum of four positive symptoms (suspiciousness, hallucinatory behavior, unusual thought content and conceptual disorganization) of 18 items in BPRS.

There was no significant difference between the four groups in gender. Age at onset was nearly significantly earlier in the TR patients, consistent with previous studies.[25] There were significantly more NTR than TR patients who were schizoaffective (chi-square=9.554, p=0.002 in the GWAS sample and the replication sample; chi-square=5.595, p=0.018).

3.2 Association Study

SNPs which differentiated TR and NTR schizophrenia by allelic association test were identified by p values and were readily distinguished by Manhattan plot and Q-Q plot (see FIG. 1). No SNP associated with TR met genome-wide significance. Six SNPs with unadjusted $P<10^{-5}$ remained after relaxing the corrected p value for FDR-BH to 0.56 (see Table 2).

TABLE 2

Summary of Top SNPs associated with TR with p < 0.0001 under allelic
association test (LD pruned). SNP position is based on NCBI Build 36.3 (HG18).

| SNP ID | Chr | Position | Minor/Major | NTR (allele count & frequency) | TR (allele count & frequency) | P (allelic) | OR (allelic) | P (trend) |
|---|---|---|---|---|---|---|---|---|
| rs2237457 | 7 | 50693638 | T/C | 48/142 (0.2526) | 77/81 (0.4873) | 5.53E-06 | 2.81 | 1.66E-05 |
| rs10825879 | 10 | 58181097 | A/G | 93/97 (0.4895) | 40/118 (0.2532) | 6.28E-06 | 0.35 | 7.29E-06 |
| rs1421321 | 7 | 154999511 | T/C | 37/153 (0.1947) | 65/91 (0.4167) | 6.64E-06 | 2.95 | 2.41E-05 |
| rs6763175 | 3 | 5402178 | G/A | 51/139 (0.2684) | 79/79 (0.5) | 8.74E-06 | 2.73 | 8.13E-06 |
| rs6500291 | 16 | 48712314 | G/A | 69/121 (0.3632) | 24/134 (0.1519) | 9.25E-06 | 0.31 | 8.12E-06 |
| rs6924295 | 6 | 46711646 | T/C | 28/162 (0.1474) | 55/103 (0.3481) | 1.22E-05 | 3.09 | 6.41E-06 |
| rs9675544 | 18 | 42570717 | A/G | 56/134 (0.2947) | 17/141 (0.1076) | 1.96E-05 | 0.29 | 5.32E-05 |
| rs7085850 | 10 | 90801279 | C/T | 45/145 (0.2368) | 71/87 (0.4494) | 2.82E-05 | 2.63 | 9.21E-05 |
| rs7933576 | 11 | 122481663 | T/C | 6/182 (0.03191) | 25/131 (0.1603) | 3.50E-05 | 5.79 | 5.06E-05 |
| rs10047718 | 13 | 21172442 | C/T | 62/128 (0.3263) | 86/72 (0.5443) | 4.22E-05 | 2.47 | 9.89E-05 |
| rs6043303 | 20 | 15402466 | G/A | 11/179 (0.05789) | 32/126 (0.2025) | 4.46E-05 | 4.13 | 5.22E-05 |
| rs9313540 | 5 | 170727300 | T/G | 54/136 (0.2842) | 17/141 (0.1076) | 4.69E-05 | 0.30 | 5.89E-05 |
| rs6432686 | 2 | 162033446 | G/A | 37/153 (0.1947) | 62/96 (0.3924) | 4.72E-05 | 2.67 | 5.88E-05 |
| rs976760 | 7 | 14240178 | T/C | 62/128 (0.3263) | 22/136 (0.1392) | 4.90E-05 | 0.33 | 7.92E-05 |
| rs7023648 | 9 | 15084374 | A/C | 95/93 (0.5053) | 46/112 (0.2911) | 5.38E-05 | 0.40 | 5.68E-05 |
| rs388033 | 6 | 167097027 | C/T | 27/163 (0.1421) | 51/107 (0.3228) | 5.72E-05 | 2.88 | 0.0001316 |
| rs4724374 | 7 | 45199367 | G/A | 10/180 (0.05263) | 30/128 (0.1899) | 6.43E-05 | 4.22 | 8.87E-05 |
| rs12510912 | 4 | 184773446 | T/C | 90/100 (0.4737) | 42/116 (0.2658) | 6.93E-05 | 0.40 | 6.88E-05 |
| rs6480553 | 10 | 73185894 | T/G | 8/182 (0.04211) | 27/131 (0.1709) | 6.98E-05 | 4.69 | 0.0001287 |
| rs12369177 | 12 | 5943781 | T/G | 85/103 (0.4521) | 39/119 (0.2468) | 7.29E-05 | 0.40 | 0.0002459 |
| rs7775338 | 6 | 57281407 | A/G | 46/144 (0.2421) | 13/145 (0.08228) | 7.62E-05 | 0.28 | 0.0001424 |
| rs6421889 | 5 | 123449176 | T/C | 87/103 (0.4579) | 40/118 (0.2532) | 7.82E-05 | 0.40 | 0.0001601 |
| rs3926649 | 15 | 88050524 | A/C | 55/135 (0.2895) | 18/138 (0.1154) | 7.84E-05 | 0.32 | 0.0001835 |
| rs12584486 | 13 | 42282533 | C/T | 14/176 (0.07368) | 35/123 (0.2215) | 7.89E-05 | 3.58 | 2.67E-05 |
| rs17776723 | 3 | 136629103 | C/T | 11/179 (0.05789) | 31/127 (0.1962) | 8.04E-05 | 3.97 | 9.84E-05 |
| rs1563817 | 15 | 21798405 | A/C | 73/117 (0.3842) | 94/64 (0.5949) | 8.95E-05 | 2.35 | 0.0001496 |
| rs9817986 | 3 | 116625629 | A/G | 42/148 (0.2211) | 11/147 (0.06962) | 9.06E-05 | 0.26 | 0.000234 |
| rs9818122 | 3 | 85943754 | G/A | 49/141 (0.2579) | 15/143 (0.09494) | 9.35E-05 | 0.30 | 9.69E-05 |
| rs13100616 | 3 | 179882245 | C/T | 81/109 (0.4263) | 36/122 (0.2278) | 9.54E-05 | 0.40 | 0.0001507 |
| rs7135617 | 12 | 120553388 | A/C | 98/92 (0.5158) | 48/108 (0.3077) | 9.62E-05 | 0.42 | 0.0001202 |
| rs11609649 | 12 | 84100623 | T/C | 20/170 (0.1053) | 42/116 (0.2658) | 9.73E-05 | 3.08 | 0.0002565 |
| rs9854706 | 3 | 3276678 | T/C | 97/93 (0.5105) | 48/110 (0.3038) | 9.84E-05 | 0.42 | 5.09E-05 |

| SNP ID | P (LR) | OR (LR) | Gene | Feature | Right_gene | Left_gene |
|---|---|---|---|---|---|---|
| rs2237457 | 7.64E-05 | 2.60 | GRB10 | intron | LOC100128600 | DDC |
| rs10825879 | 3.22E-05 | 0.34 | NA | NA | LOC100128586 | ZWINT |
| rs1421321 | 8.70E-05 | 2.68 | CNPY1 | intron | RBM33 | LOC644841 |
| rs6763175 | 2.32E-05 | 2.99 | NA | NA | MRPS35P1 | EDEM1 |
| rs6500291 | 1.21E-05 | 0.27 | LOC100130390 | intron | LOC390729 | HEATR3 |
| rs6924295 | 9.37E-06 | 3.85 | CYP39A1 | intron | SLC25A27 | RCAN2 |
| rs9675544 | 0.000149 | 0.30 | ST8SIA5 | intron | PIAS2 | LOXHD1 |
| rs7085850 | 0.0002022 | 2.41 | NA | NA | CH25H | FAS |
| rs7933576 | 0.0001336 | 6.59 | ASAM | intron | LOC100128242 | HSPA8 |
| rs10047718 | 0.0001522 | 2.41 | NA | NA | NA | FGF9 |
| rs6043303 | 0.0001577 | 4.45 | MACROD2 | intron | ENSAP | RPS10P2 |
| rs9313540 | 0.0002287 | 0.31 | NA | NA | NPM1/FGF18 | LOC644937 |
| rs6432686 | 0.0001564 | 2.77 | NA | NA | AHCTF1P | LOC100130761 |
| rs976760 | 0.0001394 | 0.32 | DGKB | intron | LOC100128217 | LOC100128637 |
| rs7023648 | 0.0002362 | 0.40 | NA | NA | TTC39B | PSIP1P |
| rs388033 | 0.0004294 | 2.62 | RPS6KA2 | intron | RNASET2 | LOC645468 |
| rs4724374 | 0.0001997 | 4.53 | NA | NA | LOC647102 | RAMP3 |
| rs12510912 | 0.0001683 | 0.39 | NA | NA | RWDD4A | ING2 |
| rs6480553 | 0.0007491 | 4.48 | C10orf54 | intron | PSAP | C10orf105 |
| rs12369177 | 0.0002111 | 0.41 | VWF | intron | CD9 | ANO2 |
| rs7775338 | 0.0003184 | 0.28 | NA | NA | PRIM2 | RAB23 |
| rs6421889 | 0.0002278 | 0.40 | NA | NA | ZNF608 | KRT18P16 |
| rs3926649 | 0.0003356 | 0.33 | WDR93 | intron | MESP1 | PEX11A |
| rs12584486 | 7.16E-05 | 4.44 | NA | NA | EPSTI1 | C13orf30 |
| rs17776723 | 0.0002696 | 4.16 | NA | NA | PPP2R3A | EPHB1 |
| rs1563817 | 0.0003468 | 2.28 | NA | NA | C15orf2 | NDN |
| rs9817986 | 0.001004 | 0.30 | NA | NA | GAP43 | LOC645207 |
| rs9818122 | 0.0002372 | 0.29 | CADM2 | intron | LOC728144 | LOC440970 |
| rs13100616 | 0.0002162 | 0.39 | KCNMB2 | intron | ZMAT3 | hCG_1646471 |
| rs7135617 | 9.33E-05 | 0.35 | ORAI1 | intron | MORN3 | FBXL10 |
| rs11609649 | 0.000457 | 2.96 | LRRIQ1 | intron | ALX1 | TSPAN19 |
| rs9854706 | 3.75E-05 | 0.33 | NA | NA | LOC100130207 | CRBN |

The Cochran-Armitage trend test was also performed to test for association. Rs2237457, a GRB10 SNP, one of the top hits associated with TR, resides in a well-known imprinted genomic region, 7p12.2 (GRB10-DDC), in human and mouse (more information available at GeneImprint's website). There is extensive evidence that brain-specific paternal expression of GRB10 regulates both fetal brain development[26] and subsequent 'social dominance' behavior and self-grooming.[27] Menheniott also reported genomic imprinting of DDC in heart and reciprocal allelic expression with neighboring GRB10 in mouse.[28] Therefore, due to unclear parental origin of risk allele, we reanalyze the GWAS dataset by excluding the 71 cases with heterozygous genotype for rs2237457, leaving 53 NTR cases and 50 TR cases. Interestingly, the association with TR was significantly enhanced, from $p=5.53\times10^{-6}$ with the heterozygotes to $p=4.99\times10^{-12}$, by allelic association test, and from $p=1.66\times10^{5}$ to $p=1.04\times10^{-6}$ by the Cochran-Armitage Trend test. With the allelic association test, rs2237457 survived correction for multiple testing with adjusted $p=2.74\times10^{-6}$ by Bonferroni correction and adjusted $p=1.37\times10^{-6}$ by FDR-BH correction. There were no other SNPs across the whole genome close to the same level of significance as rs2237457, or SNPs in LD with rs2237457, in a 30 kb region of GRB10. The rs2237457 genotype was used to predict TR status of 103 schizophrenia patients with homozygous genotypes. The sensitivity was 48%; the specificity was 94.34%; the positive predictive value was 88.89%; the negative predictive value was 65.79%; the positive likelihood ratio was 8.48; the negative likelihood ratio was 0.55. Thus, this method identified 48% patients with TRS, while 52% diagnosed as TRS were not identified by this allele, suggesting that at least half of TRS cases are due to other genetic variants or non-genetic influences. As will be discussed, the TRS cases identified by rs2237457 could be a subtype of TRS.

Logistic regression was performed for the association of TRS with rs2237457, after controlling for age of onset, gender, and PCA1/2 of population stratification ($p=7.64\times10^{-5}$ for all cases, $p=6.13\times10^{-5}$ for homozygous cases). None of the covariates had a significant impact on this association ($p>0.05$). QUANTO 1.2 was used to calculate the power of the test. We used a disease model with unmatched case-control ratio of 1:1.2. The mode of inheritance was log-additive. Kp=0.30 (population risk) since the prevalence of TRS in the schizophrenia population is 30%. The T allele of rs2237457 was found to have a frequency of 0.36. If each additional T allele increases the odds of having TRS by 2.60, and 79 TR cases and 95 NTR controls were genotyped, the power (chance) to detect an association with significance $p<0.01$ was 95%.

3.3 Functional Analysis of the Top Hits

Regional association plots of p values for SNPs flanking the six genomic loci highly associated with TR were performed. A highly LD haplotype region of rs10825879 was identified as associated with TR. This 390.5 kb region is between ZWINT and MIR3924. ZWINT interacts with SNAP25 and rab3c,[29] both of which have been reported to be involved in the regulation of release of neurotransmitters from presynaptic sites by synaptic vesicle exocytosis.

Another top SNP was rs1421321, located in the intron region of Cnpy1. Cnpy1 is expressed in the midbrain-hindbrain boundary in zebrafish, binds fibroblast growth factor receptor 1 (FGFR1), and plays a role in fibroblast growth factor (FGF) signaling.[30] FGF controls the growth and patterning of several brain structures, while later in life, they have been reported to regulate synaptogenesis, axonal growth, neuroprotection, learning, memory, and the maintenance and repair of neuronal tissue. Converging evidence supports a possible role in the pathophysiology of schizophrenia.[31]

EDEM1 is the closest gene to rs6763175. It protects neural cells from mitochondrial damage by paraquat[32] and has also been linked to schizophrenia in the GAIN study.[33] Another top SNP, rs6924295, was discovered in an intronic region of CYP39A1, which belongs to the category of drug metabolism. This SNP is ~15 kb upstream of SLC25A27, also called neuronal uncoupling protein 4 (UCP4). Previous studies linked a haplotype (rs3757241-rs10807344-rs9395206-rs2270450) in SLC25A27 to ultra-resistant schizophrenia (refractory to clozapine) in Caucasians, suggesting the treatment resistant may be related to mitochondrial dysfunction and oxidative stress.[9] Although this haplotype or individual SNP is not in LD with rs6924295, our data confirmed this haplotype associated with TR ($p=0.036$) and ultra-resistant TR ($p=0.03$) with borderline significance (Table 3A and Table 3B).

TABLE 3A

Haplotype (rs3757241-rs12192544-rs6901178-rs2270450) with TR.

| Haplotype | Freq. | NTR, TR Frequencies | Chi Square | P Value |
|---|---|---|---|---|
| CCAC | 0.511 | 0.568, 0.456 | 4.39 | 0.0362 |
| TCTC | 0.235 | 0.226, 0.247 | 0.202 | 0.6534 |
| CTAT | 0.199 | 0.174, 0.209 | 0.695 | 0.4046 |
| CCAT | 0.052 | 0.026, 0.089 | 6.485 | 0.0109 |

TABLE 3B

Haplotype (rs3757241-rs12192544-rs6901178-rs2270450) association with ultra-resistant schizophrenia.

| Haplotype | Freq. | CTR, CNTR Frequencies | Chi Square | P Value |
|---|---|---|---|---|
| CCAC | 0.423 | 0.281, 0.517 | 4.707 | 0.03 |
| TCTC | 0.159 | 0.125, 0.152 | 0.13 | 0.7186 |
| CTAT | 0.101 | 0.156, 0.083 | 1.145 | 0.2845 |
| CCAT | 0.086 | 0.000, 0.114 | 3.953 | 0.0468 |

*CTR represents the cases resistant to Clozapine in the TR group;
CNTR represents the cases responsive to Clozapine in the TR group.
_Patients with CTR were defined similarly to Monaffak F. et al.[8,9]

The strongest TRS association signal was observed at chromosome 7 in a functionally relevant type 2 diabetes candidate gene, GRB10. GRB10 has been shown to bind to the activated insulin receptor and acts as a negative regulator of insulin action and glucose uptake.[34] Overexpression of GRB10 in mice causes postnatal growth retardation and insulin resistance. Insulin resistance has been reported to be present in never-medicated, first episode schizophrenia patients in some[35] but not all studies.[36] This Illumina 610k SNP array contained a total of 15 SNPs in intron 4 of GRB10, 6 of which were significantly associated with TRS ($P<10^{-5}$). SNP imputation data showed 20 more SNPs in this region of intron 4 associated with TRS at a similar level of significance. All these SNPs were in high LD (r square>0.8), which lead to a conservative 30 kb region in intron 4 of GRB10. Rs2237457 provided the lowest p value for association with TRS. Previous studies showed that this SNP was strongly associated with a Type 2 diabetes trait, OGTT GAUC, from a GWAS study in an old Amish population.[37] T is the risk allele for Type 2 diabetes and is also the risk allele for TRS. A GWAS from the Framingham Heart Study 100k project demonstrated that this SNP was associated with BMI in a total of 1341 participants from 310 families having adiposity traits measured over 30 years of follow up.[38] That study suggest that rs2237457 is one of the top 500 SNPs associated with adiposity traits ($-\log_{10}$ p value=4.3). We performed a test of SNP (rs2237457) by covariate interaction through introducing an interaction term in the logistic regression model as follows: environmental factor included gender, age of onset, PCA1/2, and BMI, Y=β0+β1.ADD+β2.COV1+β3.ADD×COV1+e. For example, COV1 was the BMI of the patients (TR and NTR). The p value for β3 is 0.98 for all cases and 0.56 for cases with homozygous genotypes, suggesting that there was no significant interaction between rs2237457 and BMI. Other environmental factors alone or in combination demonstrated no interaction with rs2237457 genotype (p>0.01) in association with TR. A summary of the metabolic data is presented in Table 4.

TABLE 4

Summary of a limited number of samples with metabolic data categorized by the genotype of rs2237457.

| Metabolic Panel | TT | TC | CC |
|---|---|---|---|
| HbA1C | n = 6 | n = 24 | n = 33 |
|  | 5.43 (0.30) | 5.55 (0.14) | 5.41 (0.12) |
| Fasting Glucose | n = 5 | n = 26 | n = 31 |
|  | 82.4 (19.4) | 104.7 (8.5) | 98.9 (7.81) |
| BMI | n = 48 | n = 117 | n = 123 |
|  | 28.61 (1.04) | 29.39 (0.67) | 28.16 (0.65) |
| Total Cholesterol | n = 6 | n = 27 | n = 36 |
|  | 193.67 (17.53) | 173.19 (8.27) | 181.06 (7.16) |
| HDL | n = 7 | n = 27 | n = 35 |
|  | 41.57 (5.02) | 45.08 (2.56) | 42.86 (2.25) |
| LDL | n = 5 | n = 26 | n = 34 |
|  | 108.4 (14.99) | 95.15 (6.57) | 107.47 (5.75) |
| Triglyceride | n = 7 | n = 28 | n = 36 |
|  | 213.43 (39.03) | 159.68 (19.52) | 153.89 (17.21) |
| Triglyceride/HDL | n = 7 | n = 27 | n = 35 |
|  | 5.51 (1.50) | 3.75 (0.77) | 4.55 (0.67) |

Levene's Test showed equality of error variances across all parameters except LDL.
Data was presented as mean (SE).

One third of the patients had fasting blood glucose and HgA1C level data. No significant interactions between rs2237457 and fasting glucose or HgA1C was found. ANCOVA was also used to evaluate the genotypic effect of rs2237457 on baseline metabolic measures, including BMI, HgA1C, fasting blood glucose, high-density lipoprotein (HDL), low-density lipoprotein (LDL), triglyceride (TG), TG/HDL, and total cholesterol levels, using gender as a covariate. ANCOVA showed no significant interaction between gender and metabolic measures. The main effect of rs2237457 genotype (TT, TC, CC) on all metabolic measures was not statistically significant (p>0.05). Hence, rs2237457's contribution to the TRS trait was independent of adiposity or diabetes traits.

We also noted that this 30 kb haplotype resides in 70 kb upstream of the closest gene, dopa decarboxylase (DDC). DDC, also known as aromatic L-amino acid decarboxylase (AADC), catalyzes the decarboxylation of L-3,4-dihydroxyphenylalanine (DOPA) to dopamine (DA), L-5-hydroxytryptophan to serotonin (5-HT), and L-tryptophan to tryptamine. There is extensive information related DDC to schizophrenia.[39-44] This will be discussed subsequently.

3.4 Cis eQTL Analysis with Braincloud

Figure 2:
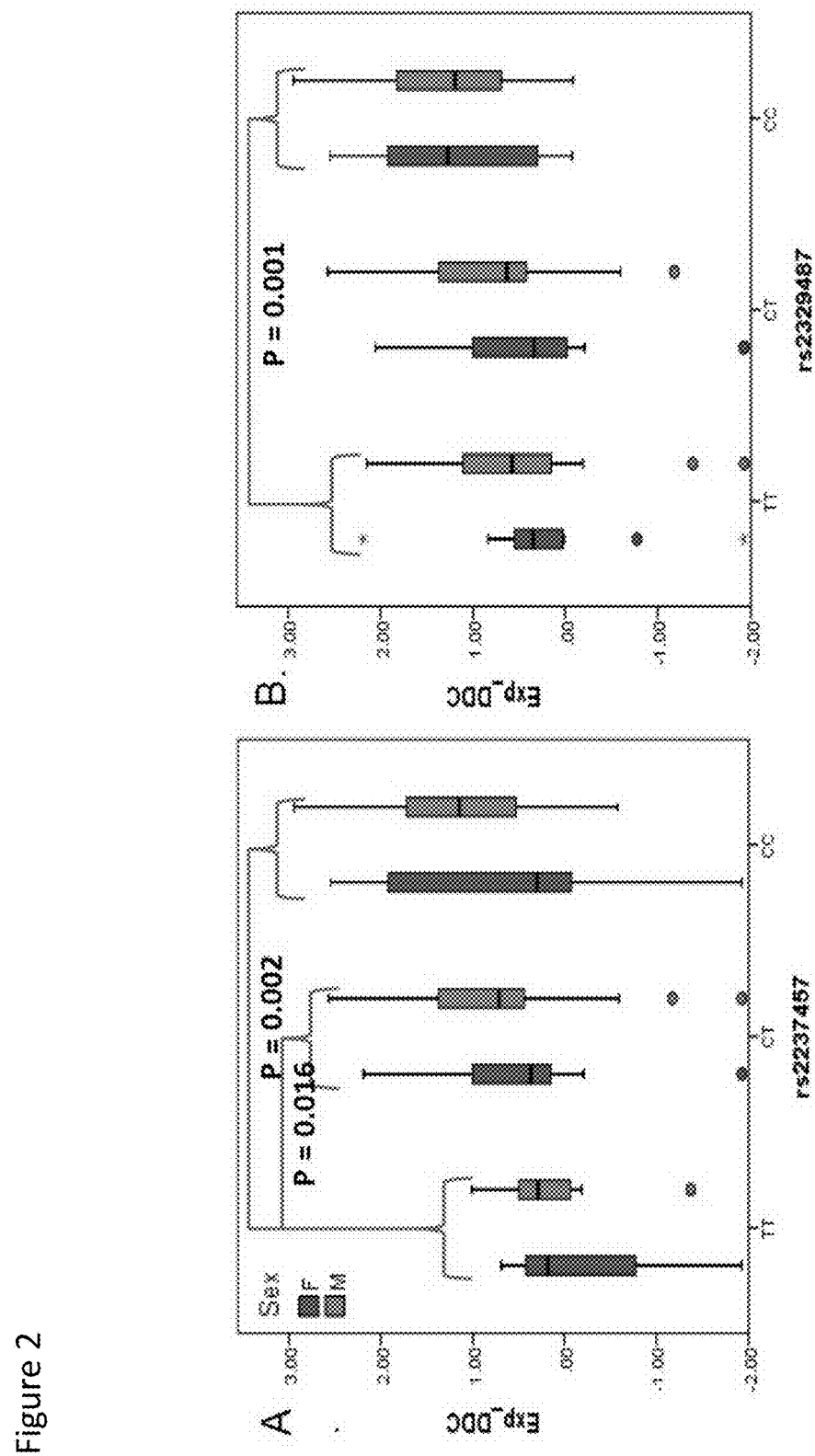
FIG. 2. BrainCloud suggests that this TR associated SNP or haplotype in an intron region of GRB10 is cis eQTL for gene expression of DDC. Box plot illustrated gene expression (normalized) of DDC (A, B) or GRB100 (C, D) as a function of genotype for SNPs, rs2237457 (A, C) or rs2329487 (B, D) across all ages of postnatal Caucasian subjects. ANOVA test was performed and only p<0.05 was presented. F=Female (left bar); M=Male (right bar).
Figure 2:
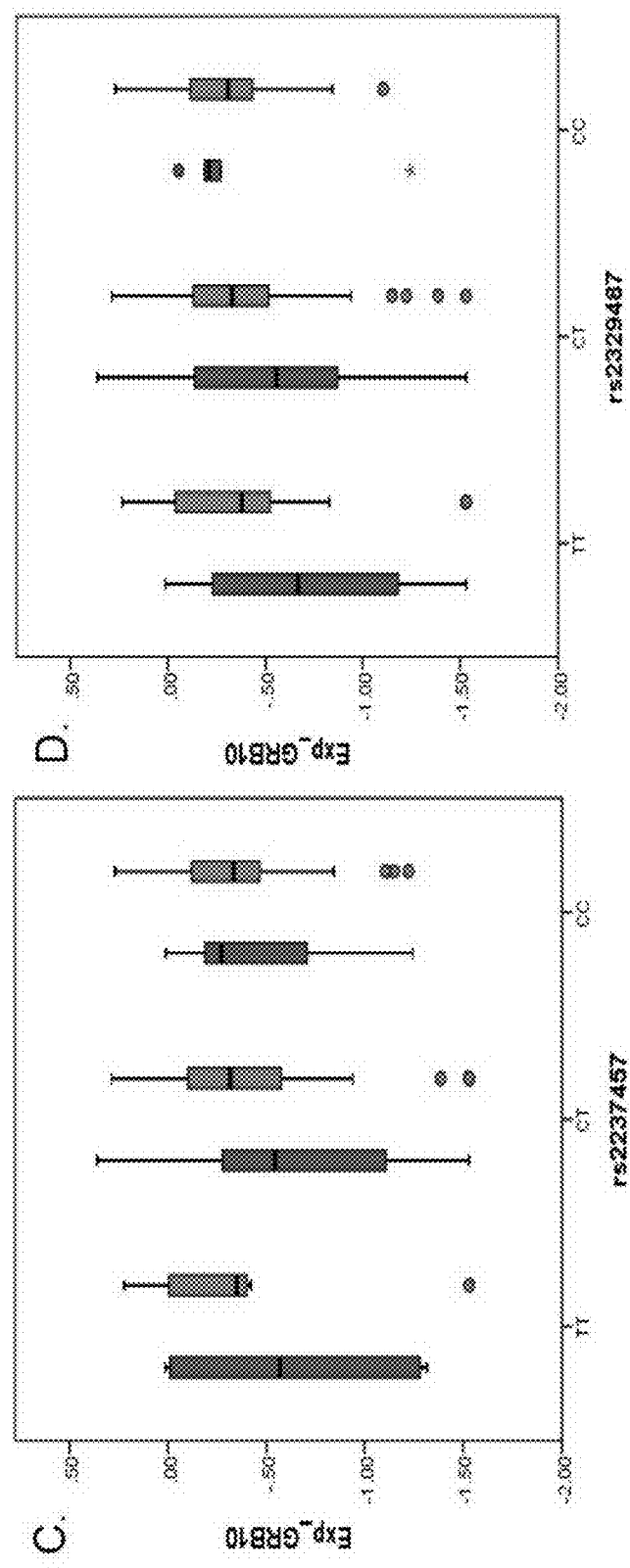

The cis eQTL analysis included all SNP loci available within a 200 kb interval (100 kb up and downstream of rs2237457) with transcripts in the BrainCloud database. Single expression probes selected for DDC or GRB10 were located in the 3' end of mRNA. For the cis association analysis, there were 105 and 130 SNPs within the 200 kb interval for DDC and GRB10, respectively. As shown in FIG. 2, by ANOVA, normal people with TT genotype for rs2237457 or rs2329487 have significantly lower levels of expression of DDC compared to CC (p=0.002 for rs2237457; p=0.001 for rs2329487) or CT genotypes (p=0.016 for rs2237457; p=0.225 for rs2329487). On the other hand, people with TT genotype for rs2237457 or rs2329487 have no statistically significant different expression of GRB10 when compared to CC genotype (p=0.460 for rs2237457; p=0.114 for rs2329487 or CT genotype (p=0.953 for rs2237457; p=0.642 for rs2329487). Further analysis indicated that DDC are aggregated in a small region of intron 4 of GRB10, suggesting an eQTL enrichment. These 6 SNPs completely match the SNPs associated with TR in this region. Regarding an association with GRB10, no significant cis eQTL was identified. Of the top five SNPs associated with TRS, four were confirmed to be potential cis Eqtl for nearby genes by the BrainCloud data analysis, suggesting that these functional variants associated with TRS were enriched in this study.

3.5 Joint Analysis with Additional Samples

Additional Caucasians samples (70 TR and 125 NTR) were available from two research clinics of HYM. DNA from these patients was genotyped for rs2237457 by Taqman assay. No cases with genomic DNA were excluded. There was a trend for rs2237457 to be more common in TRS in this sample, but less significant than the GWAS sample (Table 5).

TABLE 5

Summary of GWAS and joint analysis with additional samples for rs2237457.

|  |  | GWAS* | | | | Additional* | | | | Joint* | | | |
|---|---|---|---|---|---|---|---|---|---|---|---|---|---|
|  | TEST[#] | NTR | TR | CHISQ | P | NTR | TR | CHISQ | P | NTR | TR | CHISQ | P |
| All samples | GENO | 3/42/50 | 24/29/26 | 25.03 | 3.67E−06 | 13/55/57 | 15/22/33 | 5.62 | 0.060 | 16/97/107 | 39/51/59 | 25.06 | 3.61E−06 |
|  | TREND | 48/142 | 77/81 | 18.54 | 1.66E−05 | 81/169 | 52/88 | 0.801 | 0.371 | 129/311 | 129/169 | 13.64 | 0.00022 |
|  | ALLELIC | 48/142 | 77/81 | 20.65 | 5.53E−06 | 81/169 | 52/88 | 0.8983 | 0.343 | 129/311 | 129/169 | 15.25 | 9.42E−05 |
|  | DOM | 45/50 | 53/26 | 6.818 | 0.00902 | 68/57 | 37/33 | 0.04298 | 0.846 | 113/107 | 90/59 | 2.933 | 0.0868 |
|  | REC | 3/92 | 24/55 | 24.38 | 7.90E−07 | 13/112 | 15/55 | 4.438 | 0.035 | 16/204 | 39/110 | 25.02 | 5.66E−07 |
| Homozygous only | TREND | 6/100 | 48/52 | 23.85 | 1.04E−06 | 26/114 | 30/66 | 2.529 | 0.112 | 32/214 | 78/118 | 20.94 | 4.75E−06 |
|  | ALLELIC | 6/100 | 48/52 | 47.69 | 4.99E−12 | 26/114 | 30/66 | 5.058 | 0.025 | 32/214 | 78/118 | 41.88 | 9.73E−11 |

[#]Test includes Cochran-Armitage trend test (TREND), Genotypic (2 df) test (GENO), Dominant gene action (1 df) test (DOM), Recessive gene action (1 df) test (REC) in addition to the basic allelic test (ALLELIC).
*represents no significant deviation from Hardy-Weinberg Equilibrium (P < $10^{-2}$) in this dataset for rs2237457.
Data in NTR/TR reprssents the number of casss with the corresponding genotypes as TT/TC/CC, T/C, or TT/CC.

Nevertheless, after the two sample were combined (TR=149; NTR=220), as shown in Table 5, rs2237457 remained significantly associated with TR. The % TT in the entire TRS sample (66.1%) was significantly higher than that in the NTR sample (15.0%). We calculated that each additional T allele increased the odds of being TRS by 1.74 (odds ratio in additive mode). With genotype data from 149 TRS cases and 220 NTR controls, with significance p<0.01, the power to detect an association was 79%.

4. Discussion 4.1 Subtyping TR Schizophrenia, First-Episode and Late-Onset

The main finding of this study was identification of a possible biomarker for TRS based upon a GWAS: rs2237457 and its flanking 30 kb haplotype inside GRB10, which is upstream of DDC, a gene linked to the synthesis of the neurotransmitters DA, norepinephrine (NE), 5-HT, trace amines, and the action of antipsychotic drugs. Thus, there is a plausible biological connection between TRS and DDC. The association between this marker and IRS status was tested in a second sample which produced a weaker result, but in the same direction. The allelic test of the combined sample of patients homozygous for the risk allele, justified because parental imprinting invalidated the classification of heterozygotes, met genome wide significance, $p=9.73\times10^{11}$. These results also reflect genetic heterogeneity, such that some TRS patients have an etiologically distinct form of TRS. When a common genetic feature such as the locus in GRB10-DDC identified in this study exerts more influence than individual heterogeneity, this shared genetic liability opens up the possibility of genetically-based prediction and refinement in diagnosis. We identified one subgroup (TT) of TRS. The remainder, i.e. all CC and some TC individuals, represent one or more additional types of TRS. Thus, TRS is a complex trait. The definitional lack of response of positive symptoms to APDs in TRS patients is not explained by APD dosage, drug metabolism, pharmacokinetic differences, environmental, or other non-genetic factors, alone or in combination. Therefore, it is reasonable to hypothesize that some TRS patients represent a biologically, and, possibly, genetically distinct group, since there is evidence that positive symptoms in patients with schizophrenia,[45] and response of positive symptoms to APD treatment[46,47] are likely to be heritable. This is most likely to be the case for first-episode TR patients who never respond to APDs at adequate dosages, as opposed to the subset of treatment resistant patients who initially experience improvement in positive symptoms during treatment with APDs, but subsequently become refractory, so-called late-onset TR. These two types of TRS patients have been previously discussed.[43] In this study, we did not stratify the TR cases based on this dimension due to lack of data.

Several lines of evidence suggest a complicated link between type 2 diabetes or impaired glucose metabolism and schizophrenia[35,36,48-52] However, in this study, we did not observe a significant impact of rs2237457 genotype on metabolic measures. However, metabolic data was available for only one third of the cases, giving limited power to test the possibility of comorbidity modifying treatment resistance.

4.2 Bioinformatics Analysis on GRB10-DDC Region

Further analysis revealed that this 30 kb intronic region associated with TRS in GRB10 spans a variety of DNase I hypersensitivity clusters, suggesting a strong regulatory activity in this region, and enrichment of the modified histone mark, H3K4Me1, suggesting enhancers. According to UCSF brain methylation database,[24] the TRS associated intronic haplotype we identified harbors an H3K4me3 site (promoter). There is a strong overlap of H3K4me3 with an unmethylated intragenic CGI, suggesting this is an alternate promoter site. This promoter site is uniquely neuronal or tissue-specific since it does not overlap with the histone methylation tracks (H3K4Me3) derived from ENCODE which has signal overlaid from nine non-neuronal cell lines from a variety of human tissues. Therefore, we propose that the sequence variation in this genetic region of GRB10 will have an impact on the neuronal specific promoter, resulting in a change of gene expression, or generate isoforms of GRB10. Many common variants associated with disease are highly likely to be expression quantitative trait loci (eQTLs). These considerations suggest that this haplotype could be a cis eQTL for GRB10, or nearby genes such as DDC.

We successfully mapped the TR-associated SNP or haplotype in this region as an exclusive cis eQTL for the target gene, DDC. Although an early genetic study did not suggest that genetic polymorphism (including ~1 kb upstream promoter region) in DDC gene is associated with liability for developing schizophrenia or bipolar disorder,[53] this 30 kb region, ~70 kb upstream of the transcriptional starting site of DDC, has never been investigated.

4.3 DDC and Trace Amines

DDC is not considered to be the rate-limiting enzyme for catecholamine or indoleamine synthesis, but is rate-limiting for the synthesis of trace amines (TAs) such as 2-phenylethylamine (2-PE), p-tyramine, and tryptamine, which are thought to present at least two orders of magnitude below the level of neurotransmitters such as DA, NE and 5-HT. TAs, through the action of trace amine-associated receptor 1 (TAAR1), are believed to function as neuromodulators to maintain neuronal activity of monoamine neurotransmitters, possibly also glutamate, within defined physiological limit.[54-57] The TAAR1 agonists have been shown to have antipsychotic activity in animal models.[57] DDC expression and activity is altered by APD administration, including clozapine, in rodents, suggesting it plays a role in response to APD treatment.[58] DDC was showed to be regulated by immediate and delayed onset mechanisms involving enzyme activation and gene expression induction.[59] Abi-Dargham summarized eight PET studies on striatal DDC activity in patients with schizophrenia using [$^{18}$F] DOPA or [$^{11}$C] DOPA.[42,60,67] Six of them reported increased DDC activity.[42,62-66] As a rate-limiting enzyme for all TAs synthesis, DDC activity could play a critical role in determining response to APDs.

A deficit in DDC activity in a subgroup of TR schizophrenia leading to inadequate stimulation of TAAR1 could contribute to inadequate response to APDs. If so, TAAR1 agonists may be expected to be particularly useful in the treatment of TRS patients. The limitations in this study include a relatively small number of subjects, and the absence of data in ethnic groups other than Caucasians. In summary, this is the first GWAS study of TRS in Caucasians. We have identified a novel genetic signature for some TRS patients and a genetic marker in 7p12.2 region, which may provide an initial screening test to identify some TR Caucasian schizophrenia.

5. Supplemental Material:

5.1 Quality Control of Genotyping Data

Quality control was done by examining a summary statistics of PLINK. Estimation of IBD sharing (relatedness) was done in order to avoid the cases from most recent common ancestor in homogeneous random mating population. All 174 cases were considered as unrelated Individuals based on the pairwise IBD values greater than 0.025 as a cutoff. Only individuals and SNPs meeting the following criteria were included in further analyses. There was no flagged individual with discrepancy on gender by sex check. Call rate for individual had to be higher than 90%. Genotyping rate for each SNP had to be higher than 95%. Minor allele frequency (MAF) for each SNP had to be higher than 1%. SNPs with significant deviation from Hardy-Weinberg Equilibrium (P<10-4) were excluded. After frequency and genotyping pruning, there were 552,419 SNPs left for further analysis. Total genotyping rate in the remaining individuals was 99.9571%.

Figure 3:
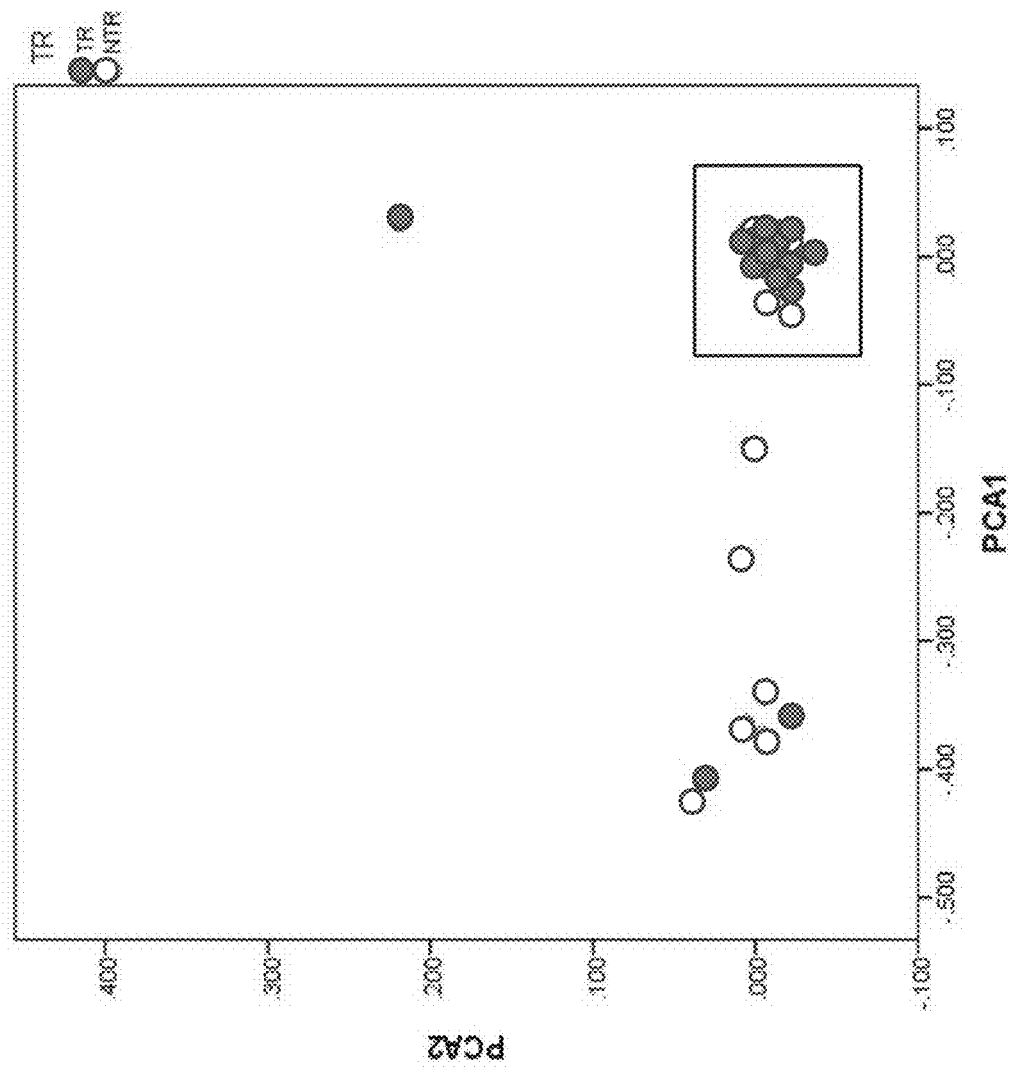
FIG. 3. Principal Component Analysis (PCA) by Eigenstrate on patients who are self described Caucasians. Majority of cases from TR and NTR groups are clustered inside of a black box.

All patients recruited in this study were self-described Caucasians. Detection of possible population stratification that might influence association analysis was carried out using principal component analysis (PCA) with genotype data for all autosome SNPs passing above QC. The PCA plot in FIG. 2 shows the first two principal components, estimated by Eigenstrate (more information available at the Eigenstrate website). No population stratification between the 79 TRS cases and 96 controls was detected (P>0.05, and Fst statistics between populations<0.001). Majority of cases from TR and NTR groups are clustered inside of the box as shown in FIG. 3 (TR=77; NTR=89).

To search for evidence of systematic bias from unrecognized population structure, analytical approach, and genotyping artifacts, Quantile-quantile (Q-Q) plots were used to examine P-value distributions. The QQ-plot showed no significant deviation from base line, suggesting that population stratification was not significant in this dataset. Genomic inflation factor based on median was 1.097 for self-described Caucasians. There was no significant improvement in this value after excluding the cases (from 1.097 to 1.090), leaving only 166 population-stratified Caucasians in the box of FIG. 3. In addition, we compared the association data from those Caucasians and that from self-described Caucasians. Top SNPs identified in this cohort also appeared to be the strongest association with TR in self-described Caucasians. This self-described population provided better power and representation of the clinical setting as we expected. Thus, all 174 cases were included for further analysis.

5.2 SNPs Interaction

Logistic regression conditioned by the target SNP was performed on all SNPs with P<$10^{-5}$ but adding the allelic dosage of one of those SNPs, for example rs2237457, as a covariate. Top SNP rs2237457 appeared to explain the multiple associated SNPs (e.g. rs2282927, rs6593077, rs2237455, rs2237468, and rs2329487) in that region of GRB10 since no significant association was left after controlling the allelic dosage of rs2237457 (Table 6A).

TABLE 6A

Logistic regression conditioned by the allele dosage of rs2237457. Only SNPs with TR-associated p < 0.0001 were included in the analysis. The p value of SNPs in the GRB10 region is presented after controlling for rs2237457.

| CHR | SNP | BP | Alleles | MAF | TEST | OR | P | Gene |
|---|---|---|---|---|---|---|---|---|
| 7 | rs2329487 | 50670014 | T/C | 0.495 | ADD | 0.7958 | 0.4555 | GRB10 |
| 7 | rs6593077 | 50673264 | A/C | 0.374 | ADD | 1.101 | 0.9025 | GRB10 |
| 7 | rs2282927 | 50687765 | C/A | 0.361 | ADD | NA | NA | GRB10 |
| 7 | rs2237455 | 50691623 | T/C | 0.391 | ADD | 1.2486 | 0.7277 | GRB10 |
| 7 | rs2237457 | 50693638 | T/C | 0.363 | ADD | NA | NA | GRB10 |
| 7 | rs2237468 | 50701856 | T/C | 0.246 | ADD | 0.6673 | 0.2374 | GRB10 |

In addition, we did conditional haplotype testing. Given these six SNPs were in high LD, we explicitly modeled the haplotypic association with TR. Likelihood ratio test suggested that the overall variation at this locus of GRB10 appeared to significantly influence the TR trait., with p=9.10×$10^{-4}$ (all cases) and p=2.42×$10^{-5}$ (homozygous cases only) (Table 6B).

TABLE 6B

Conditional haplotype test for six SNPs listed in Table 6A. Two common haplotypes (MHF ≥ 0.01) from 64 possible haplotypes were tested. Data is presented as (all cases)(homozygous cases only).

| Haplotype* | Frequency | OR (A) | OR(A) |
|---|---|---|---|
| TACTTT | 0.231/0.182 | (-ref-) | 2.83/9.425 |
| TACTTC | 0.129/0.0909 | 1.338/1.64 | |
| TCATCC | 0.0137/0.0182 | 7.407/7.438 | |
| TCACCC | 0.107/0.114 | 1.951/2.251 | |
| CCACCC | 0.494/0.573 | 2.794/4.684 | 2.09/3.021 |

*Haplotype was assemble as rs2329487-rs-2282927-rs2237457-rs2237468, based on the order of genomic position.
Odds ratio (OR) for alternate model (A) is listed in column 4.

There was no independent effect from the six SNPs after testing each individual SNP against haplotypic background (p>0.1 or identical model), suggesting that the weaker association at nearby rs2237457 did not represent an independent signal. When a specific haplotype, CCACCC, with the higher frequency (0.494/0.573), was compared to the rest of other haplotypes, the likelihood ratio test was p=3.64×$10^{-4}$ (OR=2.09) for all cases and p=3.88×$10^{-6}$ (OR=3.021) for homozygous cases only. When TACTTT was singled out, the likelihood ratio test gave p=5.82×$10^{-6}$ (OR=2.83) for all cases and p=4.91×$10^{-6}$ (OR=9.425) for homozygous cases.

In addition, we noted that other top hits with p<$10^{-5}$ such as rs10825879, rs6500291, rs6763175, still maintained the most significant associations with TR after adjustment for the allelic dosage of rs2237457, suggesting that rs2237457 alone only contributed part of the genetic association with TR trait (Table 6C).

TABLE 6C

Logistic regression conditioned by the allele dosage of rs2237457. Only SNPs with TR-associated p < 0.0001 were included in the analysis. The p value of SNPs other than those in the GRB10 region is presented after controlling for rs2237457.

| CHR | SNP | BP | Alleles | TEST | OR | P | Gene | Feature | Left_gene | Right_gene |
|---|---|---|---|---|---|---|---|---|---|---|
| 13 | rs678603 | 21177516 | A/G | ADD | 3.695 | 6.23E-06 | NA | NA | FGF9 | FTHL7 |
| 6 | rs6924295 | 46711646 | A/G | ADD | 0.2584 | 1.68E-05 | CYP39A1 | intron | RCAN2 | SLC25A27 |
| 16 | rs6500291 | 48712314 | C/T | ADD | 3.718 | 2.43E-05 | LOC100130390 | intron | HEATR3 | LOC390729 |
| 10 | rs10825879 | 58181097 | C/T | ADD | 3.128 | 2.94E-05 | NA | NA | ZWINT | LOC100128586 |
| 3 | rs6763175 | 5402178 | A/G | ADD | 0.3248 | 3.43E-05 | NA | NA | EDEM1 | MRPS35P1 |
| 9 | rs4741690 | 2372247 | C/T | ADD | 0.3503 | 4.25E-05 | NA | NA | SMARCA2 | FLJ35024 |
| 4 | rs12510912 | 184773446 | A/G | ADD | 2.993 | 5.68E-05 | NA | NA | ING2 | RWDD4A |
| 8 | rs2078674 | 143925235 | G/T | ADD | 2.885 | 7.22E-05 | GML | utr-3 | LY6D | CYP11B1 |
| 14 | rs7141881 | 93653617 | A/G | ADD | 0.3265 | 9.38E-05 | NA | NA | IFI27 | IFI27L2 |

In other words, combined the genetic risk from all top hits would provide a better marker for genetic prediction of TR. Only the top 32 SNPs (LD prune) with $p<10^{-4}$ was included in Epistasis analysis with the default parameter. There was no significant epistasis event identified with default $p<10^{-4}$ (Table 6D).

TABLE 6D

Epistasis on top TR-associated SNPs with p < 0.0001. The interaction is listed with $P_{inter}$ < 0.01.

| SNP1 | Chr_1 | Alleles_1 | Gene (Region) Name_1 | SNP2 | Chr_2 | Alleles_2 | Gene (Region) Name_2 | OR_INT | $P_{inter}$ |
|---|---|---|---|---|---|---|---|---|---|
| rs6432686 | 2 | C/T | LOC100130761-AHCTF1P | rs6500291 | 16 | C/T | LOC100130390 | 0.1971 | 0.003965 |
| rs9817986 | 3 | C/T | ZBTB20-GAP43 | rs7135617 | 12 | G/T | ORAI1 | 0.1572 | 0.000323 |
| rs6421889 | 5 | A/G | KRT18P16-ZNF608 | rs976760 | 7 | A/G | DGKB | 0.314 | 0.009551 |
| rs6421889 | 5 | A/G | KRT18P16-ZNF608 | rs6500291 | 16 | C/T | LOC100130390 | 4.759 | 0.005528 |
| rs6924295 | 6 | A/G | CYP39A1 | rs6043303 | 20 | A/G | MACROD2 | 6.654 | 0.004672 |
| rs7023648 | 9 | G/T | PSIP1P-TTC39B | rs11218985 | 11 | C/T | ASAM | 0.169 | 0.00807 |
| rs7023648 | 9 | G/T | PSIP1P-TTC39B | rs7933576 | 11 | C/T | ASAM | 0.1748 | 0.009334 |

REFERENCES

1. Tiihonen J, Wahlbeck K, Lonnqvist J, Klaukka T, Ioannidis J P, Volavka J, et al. Effectiveness of antipsychotic treatments in a nationwide cohort of patients in community care after first hospitalisation due to schizophrenia and schizoaffective disorder: observational follow-up study. BMJ 2006; 333(7561): 224.
2. Conley R R, Kelly D L. Management of treatment resistance in schizophrenia. Biological psychiatry 2001; 50(11): 898-911.
3. Essock S M, Hargreaves W A, Dohm F A, Goethe J, Carver L, Hipshman L. Clozapine eligibility among state hospital patients. Schizophrenia bulletin 1996; 22(1): 15-25.
4. Juarez-Reyes M G, Shumway M, Battle C, Bacchetti P, Hansen M S, Hargreaves W A. Effects of stringent criteria on eligibility for clozapine among public mental health clients. Psychiatr Serv 1995; 46(8): 801-806.
5. Kane J, Honigfeld G, Singer J, Meltzer H. Clozapine for the treatment-resistant schizophrenic. A double-blind comparison with chlorpromazine. Archives of general psychiatry 1988; 45(9): 789-796.
6. Kane J M, Honigfeld G, Singer J, Meltzer H. Clozapine in treatment-resistant schizophrenics. Psychopharmacology bulletin 1988; 24(1): 62-67.
7. Meltzer H Y. Treatment-resistant schizophrenia—the role of clozapine. Current medical research and opinion 1997; 14(1): 1-20.
8. Mouaffak F, Kebir O, Chayet M, Tordjman S, Vacheron M N, Millet B, et al. Association of Disrupted in Schizophrenia 1 (DISC1) missense variants with ultra-resistant schizophrenia. The pharmacogenomics journal 2011; 11(4): 267-273.
9. Mouaffak F, Kebir O, Bellon A, Gourevitch R, Tordjman S, Viala A, et al. Association of an UCP4 (SLC25A27) haplotype with ultra-resistant schizophrenia. Pharmacogenomics 2011; 12(2): 185-193.
10. Mundo E, Altamura A C, Vismara S, Zanardini R, Bignotti S, Randazzo R, et al. MCP-1 gene (SCYA2) and schizophrenia: a case-control association study. American journal of medical genetics Part B, Neuropsychiatric genetics: the official publication of the International Society of Psychiatric Genetics 2005; 132B(1): 1-4.
11. Kohlrausch F B, Gama C S, Lobato M I, Belmonte-de-Abreu P. Callegari-Jacques S M, Gesteira A, et al. Naturalistic pharmacogenetic study of treatment resistance to typical neuroleptics in European-Brazilian schizophrenics. Pharmacogenetics and genomics 2008; 18(7): 599-609.
12. Joober R, Benkelfat C, Brisebois K, Toulouse A, Turecki G, Lal S, et al. T102C polymorphism in the 5HT2A gene and schizophrenia: relation to phenotype and drug response variability. Journal of psychiatry & neuroscience: JPN 1999; 24(2): 141-146.
13. Ji X, Takahashi N, Saito S, Ishihara R, Maeno N, Inada T, et al. Relationship between three serotonin receptor subtypes (HTR3A, HTR2A and HTR4) and treatment-resistant schizophrenia in the Japanese population. Neuroscience letters 2008; 435(2): 95-98.
14. Ji X, Takahashi N, Branko A, Ishihara R, Nagai T, Mouri A, et al. An association between serotonin receptor 3B gene (HTR3B) and treatment-resistant schizophrenia (TRS) in a Japanese population. *Nagoya journal of medical science* 2008; 70(1-2): 11-17.
15. Liou Y J, Wang H H, Lee M T, Wang S C, Chiang H L, Chen C C, et al. Genome-wide association study of treatment refractory schizophrenia in Han Chinese. *PloS one* 2012; 7(3): e33598.
16. Jia P, Jayathilake K, Zhao Z, Meltzer H Y. Association of FAS, a TNF-alpha receptor gene, with treatment resistant schizophrenia. *Schizophrenia research* 2011; 129(2-3): 211-212.
17. Zhang J P, Lencz T, Geisler S, Derosse P, Bromet E J, Malhotra A K. Genetic variation in BDNF is associated with antipsychotic treatment resistance in patients with schizophrenia. *Schizophrenia research* 2013.
18. Bilder R M, Wu H, Bogerts B, Degreef G, Ashtari M, Alvir J M, et al. Absence of regional hemispheric volume asymmetries in first-episode schizophrenia. *The American journal of psychiatry* 1994; 151(10): 1437-1447.
19. Stem R G, Kahn R S, Davidson M. Predictors of response to neuroleptic treatment in schizophrenia. *The Psychiatric clinics of North America* 1993; 16(2): 313-338.
20. Roussos P, Katsel P, Davis K L, Siever L J, Haroutunian V. A system-level transcriptomic analysis of schizophrenia using postmortem brain tissue samples. *Archives of general psychiatry* 2012; 69(12): 1205-1213.
21. Arnold S E, Rioux L. Challenges, status, and opportunities for studying developmental neuropathology in adult schizophrenia. *Schizophrenia bulletin* 2001; 27(3): 395-416.
22. Colantuoni C, Lipska B K, Ye T, Hyde T M, Tao R, Leek J T, et al. Temporal dynamics and genetic control of transcription in the human prefrontal cortex. *Nature* 2011; 478(7370): 519-523.
23. Purcell S M, Wray N R, Stone J L, Visscher P M, O'Donovan M C, Sullivan P F, et al. Common polygenic variation contributes to risk of schizophrenia and bipolar disorder. *Nature* 20 460(7256): 748-752.
24. Maunakea A K, Nagarajan R P, Bilenky M, Ballinger T J, D'Souza C, Fouse S D, et al. Conserved role of intragenic DNA methylation in regulating alternative promoters. *Nature* 2010; 466(7303): 253-257.
25. Meltzer H Y, Lee M, Cola P. The evolution of treatment resistance: biologic implications. *Journal of clinical psychopharmacology* 1998; 18(2 Suppl 1): 5S-11S.
26. Amaud P, Monk D. Hitchins M, Gordon E, Dean W, Beechey C V, et al. Conserved methylation imprints in the human and mouse GRB10 genes with divergent allelic expression suggests differential reading of the same mark. *Human molecular genetics* 2003; 12(9): 1005-1019.
27. Garfield A S, Cowley M, Smith F M, Moorwood K, Stewart-Cox J E, Gilroy K. et al. Distinct physiological and behavioural functions for parental alleles of imprinted Grb10. *Nature* 2011; 469(7331): 534-538.
28. Menheniott T R, Woodfine K, Schulz R, Wood A J, Monk D, Giraud A S, et al. Genomic imprinting of Dopa decarboxylase in heart and reciprocal allelic expression with neighboring Grb10. *Molecular and cellular biology* 2008; 28(1): 386-396.
29. van Vlijmen T, Vleugel M, Evers M, Mohammed S, Wulf P S, Heck A J, et al. A unique residue in rab3c determines the interaction with novel binding protein Zwint-1. *FEBS letters* 2008; 582(19): 2838-2842.
30. Hirate Y, Okamoto H. Canopyl, a novel regulator of FGF signaling around the midbrain-hindbrain boundary in zebrafish. *Current biology: CB* 2006; 16(4): 421-427.
31. Terwisscha van Scheltinga A F, Bakker S C, Kahn R S. Fibroblast growth factors in schizophrenia. *Schizophrenia bulletin* 2010; 36(6): 1157-1166.
32. Yang W, Tiffany-Castiglioni E, Koh H C, Son I H. Paraquat activates the IRE1/ASK1/JNK cascade associated with apoptosis in human neuroblastoma SH-SY5Y cells. *Toxicology letters* 2009; 191(2-3): 203-210.
33. Glessner J T, Reilly M P, Kim C E, Takahashi N, Albano A, Hou C, et al. Strong synaptic transmission impact by copy number variations in schizophrenia. *Proceedings of the National Academy of Sciences of the United States of America* 2010; 107(23): 10584-10589.
34. Wang L, Balas B, Christ-Roberts C Y, Kim R Y, Ramos F J, Kikani C K, et al. Peripheral disruption of the Grb10 gene enhances insulin signaling and sensitivity in vivo. *Molecular and cellular biology* 2007; 27(18): 6497-6505.
35. Ryan M C, Collins P, Thakore J H. Impaired fasting glucose tolerance in first-episode, drug-naïve patients with schizophrenia. *The American journal of psychiatry* 2003; 160(2): 284-289.
36. Arranz B, Rosel P, Ramirez N, Duenas R, Fernandez P, Sanchez J M, et al. Insulin resistance and increased leptin concentrations in noncompliant schizophrenia patients but not in antipsychotic-naive first-episode schizophrenia patients. *The Journal of clinical psychiatry* 2004; 65(10): 1335-1342.
37. Rampersaud E, Damcott C M, Fu M, Shen H. McArdle P, Shi X, et al. Identification of novel candidate genes for type 2 diabetes from a genome-wide association scan in the Old Order Amish: evidence for replication from diabetes-related quantitative traits and from independent populations. *Diabetes* 2007; 56(12): 3053-3062.
38. Fox C S, Heard-Costa N, Cupples L A. Dupuis J, Vasan R S, Atwood L D. Genome-wide association to body mass index and waist circumference: the Framingham Heart Study 100K project. *BMC medical genetics* 2007; 8 Suppl 1: S18.
39. Borglum A D, Hampson M, Kjeldsen T E, Muir W, Murray V, Ewald H, et al. Dopa decarboxylasegenotypes may influence age at onset of schizophrenia. *Molecular psychiatry* 2001; 6(6): 712-717.
40. Grunder G, Vernaleken I, Muller M J, Davids E, Heydari N, Buchholz H G, et al. Subchronic haloperidol downregulates dopamine synthesis capacity in the brain of schizophrenic patients in vivo. *Neuropsychopharmacology: official publication of the American College of Neuropsychopharmacology* 2003; 28(4): 787-794.
41. Ikemoto K, Nishimura A, Oda T, Nagatsu I, Nishi K. Number of striatal D-neurons is reduced in autopsy brains of schizophrenics. *Leg Med (Tokyo)* 2003; 5 Suppl 1: S221-224.
42. Reith J, Benkelfat C, Sherwin A, Yasuhara Y, Kuwabara H, Andermann F, et al. Elevated dopa decarboxylase activity in living brain of patients with psychosis. *Proceedings of the National Academy of Sciences of the United States of America* 1994; 91(24): 11651-11654.
43. O'Reilly R, Davis B A, Durden D A, Thorpe L, Machnee H, Boulton A A. Plasma phenylethylamine in schizophrenic patients. *Biological psychiatry* 1991: 30(2): 145-150.
44. Davis B A, Shrikhande S, Paralikar V P, Hirsch S R, Durden D A, Boulton A A. Phenylacetic acid in CSF and serum in Indian schizophrenic patients. *Progress in neuro-psychopharmacology, & biological psychiatry* 1991; 15(1): 41-47.
45. Dworkin R H, Lenzenweger M F, Moldin S O, Skillings G F, Levick S E. A multidimensional approach to the genetics of schizophrenia. *The American journal of psychiatry* 1988; 145(9): 1077-1083.
46. Hitzemann R, Dains K, Bier-Langing C M, Zahniser N R. On the selection of mice for haloperidol response and non-response. *Psychopharmacology* 1991; 103(2): 244-250.
47. Northup A, Nimgaonkar V L. Genetics of schizophrenia: implications for treatment. *Expert review of neurotherapeutics* 2004; 4(4): 725-731.
48. Adkins D E, Aberg K, McClay J L, Bukszar J, Zhao Z, Jia P, et al. Genomewide pharmacogenomic study of metabolic side effects to antipsychotic drugs. *Molecular psychiatry* 2011; 16(3): 321-332.
49. Mukherjee S, Schnur D B, Reddy R. Family history of type 2 diabetes in schizophrenic patients. *Lancet* 1989; 1(8636): 495.
50. Bushe C, Holt R. Prevalence of diabetes and impaired glucose tolerance in patients with schizophrenia. *The British journal of psychiatry Supplement* 2004; 47: S67-71.
51. Liu Y, Li Z, Zhang M, Deng Y, Yi Z, Shi T. Exploring the pathogenetic association between schizophrenia and type 2 diabetes mellitus diseases based on pathway analysis. *BMC medical genomics* 2013; 6 Suppl 1: S17.
52. Oresic M, Tang J, Seppanen-Laakso T, Mattila I, Saarni S E, Saarni S I, et al. Metabolome in schizophrenia and other psychotic disorders: a general population-based study. *Genome medicine* 2011; 3(3): 19.
53. Speight G, Turic D, Austin J, Hoogendoorn B, Cardno A G, Jones I., et al. Comparative sequencing and association studies of aromatic L-amino acid decarboxylase in schizophrenia and bipolar disorder. *Molecular psychiatry* 2000; 5(3): 327-331.
54. Berry M D. The potential of trace amines and their receptors for treating neurological and psychiatric diseases. *Reviews on recent clinical trials* 2007; 2(1): 3-19.
55. Revel F G, Moreau J L, Gainetdinov R R, Bradaia A, Sotnikova T D, Mory R. et al. TAAR1 activation modulates monoaminergic neurotransmission, preventing hyperdopaminergic and hypoglutamatergic activity. *Proceedings of the National Academy of Sciences of the United States of America* 2011; 108(20): 8485-8490.
56. Miller G M. The emerging role of trace amine-associated receptor 1 in the functional regulation of monoamine transporters and dopaminergic activity. *Journal of neurochemistry* 2011; 116(2): 164-176.
57. Revel F G, Moreau J L, Pouzet B, Mory R, Bradaia A, Buchy D, et al. A new perspective for schizophrenia: TAAR1 agonists reveal antipsychotic- and antidepressant-like activity, improve cognition and control body weight. *Molecular psychiatry* 2013; 18(5): 543-556.
58. Neff N H, Wemlinger T A, Duchemin A M, Hadjiconstantinou M. Clozapine modulates aromatic Lamino acid decarboxylase activity in mouse striatum. *The Journal of pharmacology and experimental therapeutics* 2006; 317 (2): 480-487.
59. Neff N H, Wemlinger T A, Hadjiconstantinou M. SCH 23390 enhances exogenous L-DOPA decarboxylation in nigrostriatal neurons. *J Neural Transm* 2000; 107(4): 429-443.
60. Dao-Castellana M H, Paillere-Martinot M L, Hantraye P, Attar-Levy D, Remy P, Crouzel C, et al. Presynaptic dopaminergic function in the striatum of schizophrenic patients. *Schizophrenia research* 1997; 23(2): 167-174.
61. Elkashef A M, Doudet D, Bryant T, Cohen R M, Li S H, Wyatt R J. 6-(18)F-DOPA PET study in patients with schizophrenia. Positron emission tomography. *Psychiatry research* 2000; 100(1): 1-11.
62. Hietala J, Syvalahti E, Vilkman H, Vuorio K, Rakkolainen V, Bergman J, et al. Depressive symptoms and presynaptic dopamine function in neuroleptic-naive schizophrenia. *Schizophrenia research* 1999; 35(1): 41-50.
63. Hietala J, Syvalahti E, Vuorio K, Rakkolainen V, Bergman J, Haaparanta M, et al. Presynaptic dopamine function in striatum of neuroleptic-naive schizophrenic patients. *Lancet* 1995; 346(8983): 1130-1131.
64. Lindstrom L H, Gefvert O, Hagberg G, Lundberg T, Bergstrom M, Hartvig P, et al. Increased dopamine synthesis rate in medial prefrontal cortex and striatum in schizophrenia indicated by L-(beta-11C) DOPA and PET. *Biological psychiatry* 1999; 46(5): 681-688.
65. McGowan S, Lawrence A D, Sales T, Quested D, Grasby P. Presynaptic dopaminergic dysfunction in schizophrenia: a positron emission tomographic [18F]fluorodopa study. *Archives of general psychiatry* 2004; 61(2): 134-142.
66. Meyer-Lindenberg A, Miletich R S, Kohn P D, Esposito G, Carson R E, Quarantelli M, et al. Reduced prefrontal activity predicts exaggerated striatal dopaminergic function in schizophrenia. *Nature neuroscience* 2002; 5(3): 267-271.
67. Guillin O, Abi-Dargham A, Laruelle M. Neurobiology of dopamine in schizophrenia. *International review of neurobiology* 2007; 78: 1-39.
68. Need A C, et al. A Genome-Wide Investigation of SNPs and CNVs in Schizophrenia. *PLoS Genet.* 2009 March; 5(3): 10.1371.
69. Dixon L B, et al. Conventional antipsychotic medications for schizophrenia. *Schizophrenia bulletin* 1995; 21(4): 567-577.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. A method comprising:
(a) reacting a genomic DNA sample from a patient having a psychiatric disorder with a reagent composition that comprises polynucleotide reagents for detecting the minor allele of the single nucleotide polymorphism rs2237457;

(b) detecting the minor allele of the single nucleotide polymorphism rs2237457 in the genomic DNA sample from the patient, wherein the reagent composition comprises a polynucleotide primer for sequencing the genomic DNA sample from the patient, and detecting the minor allele of the single nucleotide polymorphism rs2237457 comprises sequencing the single nucleotide polymorphism rs2237457; and (c) after detecting the minor allele of the single nucleotide polymorphism rs2237457 in the genomic DNA sample from the patient, administering a treatment to the patient consisting of administering a trace amine-associated receptor 1 (TAAR1) agonist to the patient.

2. The method of claim 1, further comprising detecting whether the patient is homozygous for the minor allele of rs2237457.

3. The method of claim 1, wherein the TAAR1 agonist is selected from a group consisting of m-tyramine, p-tyramine, phenethylamine, m-octopamine, p-octopamine, N-methylphenethylamine, N-methyltyramine, phenylethanolamine, synephrine, 3-methoxytyramine, 3-iodothyronamine, tryptamine, N-methyltryptamine, dopamine, norepinephrine, serotonin, histamine, amphetamine, methamphetamine, 3,4-methylenedioxymethamphetamine, 2,5-dimethoxy-4-iodoamphetamine, phenylpropanolamine, alpha-methylphenethylamine, beta-methylphenethylamine, N-methylphenethylamine, 2-methylphenethylamine, 3-methylphenethylamine, 4-methylphenethylamine, (S)-4-[(ethylphenylamino)methyl]-4,5-dihydrooxazol-2-ylamine (RO5166017), (4S)-4-[(2S)-2-phenylbutyl]-4,5-dihydro-1,3-oxazol-2-amine (RO5256390), (4S)-4-[3-fluoro-2methylphenyl]-4,5-dihydro-1,3-oxazol-2-amine (RO5263397), and (4S)-4-[3,4-dichlorophenyl]-4,5-dihydro-1,3-oxazol-2-amine (RO5203648).

4. The method of claim 1, wherein the reagent composition comprises polynucleotide primers for amplifying the single nucleotide polymorphism rs2237457, and detecting the single nucleotide polymorphism rs2237457 comprises amplifying the single nucleotide polymorphism rs2237457.

5. A method comprising:
(a) reacting a genomic DNA sample from a patient having a psychiatric disorder with a reagent composition that comprises polynucleotide reagents for detecting whether the patient is homozygous or heterozygous for a C-allele or a T-allele at the polymorphic position rs2237457;

(b) detecting that the patient is homozygous or heterozygous for a T-allele at the polymorphic position rs2237457, wherein the reagent composition comprises a polynucleotide primer for sequencing the genomic DNA sample, and detecting that the patient is homozygous or heterozygous for a T-allele at the polymorphic position rs2237457 comprises sequencing the polymorphic position rs2237457; and (c) after detecting that the patient is homozygous or heterozygous for a T-allele at the polymorphic position rs2237457, administering a treatment to the patient consisting of administering a trace amine-associated receptor 1 (TAAR1) agonist to the patient.

6. The method of claim 5, wherein the TAAR1 agonist is selected from a group consisting of m-tyramine, p-tyramine, phenethylamine, m-octopamine, p-octopamine, N-methylphenethylamine, N-methyltyramine, phenylethanolamine, synephrine, 3-methoxytyramine, 3-iodothyronamine, tryptamine, N-methyltryptamine, dopamine, norepinephrine, serotonin, histamine, amphetamine, methamphetamine, 3,4-methylenedioxymethamphetamine, 2,5-dimethoxy-4-iodoamphetamine, phenylpropanolamine, alpha-methylphenethylamine, beta-methylphenethylamine, N-methylphenethylamine, 2-methylphenethylamine, 3-methylphenethylamine, 4-methylphenethylamine, (S)-4-[(ethylphenyl amino)methyl]-4,5-dihydrooxazol-2-ylamine (RO5166017), (4S)-4-[(2S)-2-phenylbutyl]-4,5-dihydro-1,3-oxazol-2-amine (RO5256390), (4S)-4-[3-fluoro-2methylphenyl]-4,5-dihydro-1,3-oxazol-2-amine (RO5263397), and (4S)-4-[3,4-dichlorophenyl]-4,5-dihydro-1,3-oxazol-2-amine (RO5203648).

7. The method of claim 5, wherein the reagent composition comprises polynucleotide primers for amplifying the polymorphic position rs2237457, and detecting the polymorphic position rs2237457 comprises amplifying the polymorphic position rs2237457.

8. A method comprising:
(a) reacting a genomic DNA sample from a patient having a psychiatric disorder with a reagent composition that comprises polynucleotide reagents for detecting the minor allele of the single nucleotide polymorphism rs2237457;

(b) detecting the minor allele of the single nucleotide polymorphism rs2237457 in the genomic DNA sample from the patient, wherein the reagent composition comprises a polynucleotide probe for probing the single nucleotide polymorphism rs2237457, and detecting the minor allele of the single nucleotide polymorphism rs2237457 comprises hybridizing the polynucleotide probe to the single nucleotide polymorphism rs2237457 and detecting hybridization of the polynucleotide probe to the single nucleotide polymorphism rs2237457; and (c) after detecting the minor allele of the single nucleotide polymorphism rs2237457 in the genomic DNA sample from the patient, administering a treatment to the patient consisting of administering a trace amine-associated receptor 1 (TAAR1) agonist to the patient.

9. The method of claim 8, further comprising detecting whether the patient is homozygous for the minor allele of rs2237457.

10. The method of claim 8, wherein the TAAR1 agonist is selected from a group consisting of m-tyramine, p-tyramine, phenethylamine, m-octopamine, p-octopamine, N-methylphenethylamine, N-methyltyramine, phenylethanolamine, synephrine, 3-methoxytyramine, 3-iodothyronamine, tryptamine, N-methyltryptamine, dopamine, norepinephrine, serotonin, histamine, amphetamine, methamphetamine, 3,4-methylenedioxymethamphetamine, 2,5-dimethoxy-4-iodoamphetamine, phenylpropanolamine, alpha-methylphenethylamine, beta-methylphenethylamine, N-methylphenethylamine, 2-methylphenethylamine, 3-methylphenethylamine, 4-methylphenethylamine, (S)-4-[(ethylphenylamino)methyl]-4,5-dihydrooxazol-2-ylamine (RO5166017), (4S)-4-[(2S)-2-phenylbutyl]-4,5-dihydro-1,3-oxazol-2-amine (RO5256390), (4S)-4-[3-fluoro-2methylphenyl]-4,5-dihydro-1,3-oxazol-2-amine (RO5263397), and (4S)-4-[3,4-dichlorophenyl]-4,5-dihydro-1,3-oxazol-2-amine (RO5203648).

11. The method of claim 8, wherein the reagent composition comprises polynucleotide primers for amplifying the polymorphic position rs2237457, and detecting the polymorphic position rs2237457 comprises amplifying the polymorphic position rs2237457.

* * * * *